US012685739B2

(12) United States Patent
Simard et al.

(10) Patent No.: US 12,685,739 B2
(45) Date of Patent: Jul. 21, 2026

(54) COMPOSITIONS AND METHODS FOR TREATING LUNG INJURY

(71) Applicants: University of Maryland, Baltimore, Baltimore, MD (US); The United States Government as represented by the Department of Veterans Affairs, Washington, DC (US)

(72) Inventors: J. Marc Simard, Baltimore, MD (US); Vladimir Gerzanich, Elkridge, MD (US); Caron M. Hong, Ellicott City, MD (US)

(73) Assignees: UNIVERSITY OF MARYLAND, BALTIMORE, Baltimore, MD (US); THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 699 days.

(21) Appl. No.: 17/920,946

(22) PCT Filed: Apr. 23, 2021

(86) PCT No.: PCT/US2021/028936
§ 371 (c)(1),
(2) Date: Oct. 24, 2022

(87) PCT Pub. No.: WO2021/217063
PCT Pub. Date: Oct. 28, 2021

(65) Prior Publication Data
US 2023/0165880 A1 Jun. 1, 2023

Related U.S. Application Data

(60) Provisional application No. 63/015,293, filed on Apr. 24, 2020.

(51) Int. Cl.
*A61K 31/64* (2006.01)
*A61P 11/00* (2006.01)

(52) U.S. Cl.
CPC .............. *A61K 31/64* (2013.01); *A61P 11/00* (2018.01)

(58) Field of Classification Search
CPC ...... A61K 31/196; A61K 31/44; A61K 31/64; A61P 11/00
See application file for complete search history.

(56) References Cited

U.S. PATENT DOCUMENTS

2006/0257852 A1 11/2006 Rappuoli
2011/0263478 A1 10/2011 Simard
2022/0088039 A1* 3/2022 Jacobson ........... A61K 31/7076

FOREIGN PATENT DOCUMENTS

WO WO-2010033560 A2 * 3/2010 .............. A61P 37/08

OTHER PUBLICATIONS

Aittoniemi, 2009, Philos Trans R Soc Lond B Biol Sci . Jan. 27, 2009;364(1514):257-67 (Year: 2009).*
Ohsu, 2025, https://www.ohsu.edu/ regenerative-medicine-center/ acute-lung-injury, 2025 (Year: 2025).*
Qin, Frontiers in physiology vol. 12 731594. Oct. 26, 2021 (Year: 2021).*
Liu et al. (Inflammation, vol. 38, No. 1, 2015, p. 433-444) (Year: 2015).*
Li et al. (Clinical and Translational Medicine, Mar. 31, 2020, 10, 20-27). (Year: 2020).*
Fan et al. (JAMA, 2005, vol. 294, No. 22). (Year: 2005).*
International Search Report from Appl. No. PCT/US21/28936, mailed on Sep. 27, 2021.
Zhang et al., A Protective Role of Glibenclamide in Inflammation-Associated Injury, Mediaors of Inflamation, (2017), Article ID 3578702, 11 pages.
Wang et al., S100A8/A9 in Inflamation, Front Immunol., (2018), 9:1298, p. 1-14.
Ventilator-associated lung injury, Wikipedia, (Oct. 8, 2018), retrieved on Jun. 24, 2021 from https://en.wikipedia.org/w/index.php?title= ventilator-associated_lung_injury&oldid=863047309; p. 1-4.
COVID-19, Wikipedi, (Mar. 17, 2020), retrieved on May 7, 2021 fom https://en.wikipedia.org/w/index.php?title=COVID-19&oldid= 946010373; p. 1-27.

* cited by examiner

*Primary Examiner* — Umamaheswari Ramachandran
(74) *Attorney, Agent, or Firm* — Nevrivy Patent Law Group P.L.L.C.

(57) ABSTRACT

The present invention provides methods of reducing lung injury in a subject in need thereof, comprising administering to the subject an effective amount of an agent that inhibits the activity of SUR1.

10 Claims, 10 Drawing Sheets

Fig. 1

Naive    no MV    MV

COMPOSITIONS AND METHODS FOR TREATING LUNG INJURY

FIELD OF THE INVENTION

The field of the invention relates to medicine, therapeutics and infectious disease, in particular therapeutics for treating lung injury, acute lung injury, acute respiratory distress syndrome and ventilator induced lung injury.

BACKGROUND OF THE INVENTION

Coronaviruses (CoV) are RNA viruses that infect the respiratory, gastrointestinal and central nervous system of humans and animals (Cui et al., Nat Rev Microbiol, (2019), 17:181-192). Severe acute respiratory syndrome coronavirus (SARS-CoV) and Middle East respiratory syndrome coronavirus (MERS-CoV) are highly infectious viruses responsible for thousands of deaths in the last decades. The most recent outbreak involving SARS-CoV-2 has spread rapidly throughout the world as the Coronavirus Disease 2019 (COVID-19) pandemic (Huang et al., Lancet, (2020), 395:497-506). At present, there is no treatment for COVID-19 (Huang et al., Lancet, (2020), 395:497-506).

In patients with COVID-19 (i.e., infected by SARS-CoV-2) the disease may progress to acute lung injury (ALI) and acute respiratory distress syndrome (ARDS), leading to cardiac arrest (Huang et al., Lancet, (2020), 395:497-506; Chen et al., Lancet, (2020), 395:507-513). A substantial number of patients infected with SARS-CoV-2 progress to an ARDS, a type of severe respiratory failure characterized by the rapid onset of widespread inflammation and edema in the lungs, and is associated with high mortality. Patients with ARDS or SARS-CoV-2 infection who develop hypoxic respiratory failure require mechanical ventilation (Wujtewicz et al., Anaesthesiol Intensive Ther, (2020), 52(1):34-41; Wright et al., Emerg Med Clin North Am, (2014), 32(4):871-87). ARDS is diagnosed in 40% of SARS-CoV-2 patients treated in hospital intensive care units (ICUs), and mechanical ventilation is used in 60% of these ICU patients (Wujtewicz et al., Anaesthesiol Intensive Ther, (2020), 52(1):34-41).

There is no effective treatment for ARDS. Corticosteroids may improve survival, but this is not unambiguous, and there is no evidence that treatments with exogenous surfactants, statins, beta-blockers or n-acetylcysteine decreases early mortality, late all-cause mortality, duration of mechanical ventilation, or number of ventilator-free days (Lewis et al., Cochrane Database Syst Rev, (2019), 7(7):CD004477 doi: 10.1002/14651858.CD004477.pub3). Currently, mechanical ventilation is the only treatment available for ARDS.

Mechanical ventilation can be lifesaving, but it comes with potential complications (Brower et al., N Engl J Med, (2000), 342(18):1301-8). Mechanical ventilation itself can activate inflammatory pathways and cause pulmonary edema, a process known as ventilator-induced lung injury (VILI) (Parker et al., Crit Care Med, (1993), 21(1):131-43; Dos Santos et al., J Appl Physiol (1985), (2000) 89(4):1645-55). Almost cynically, VILI actually worsens the adverse pulmonary effects of the very disease that led to respiratory failure and mechanical ventilation in the first place (Bates et al., Ann Transl Med, (2018), 6(19):378; Ricard et al., Eur Respir J Suppl, (2003), 42:2s-9s). Since a SARS-CoV-2 infection itself causes a release of numerous pro-inflammatory cytokines, the two together, VILI plus SARS-CoV-2, leads to a hyperinflammatory milieu in the lung tissues that greatly exacerbates pulmonary dysfunction (Conti et al., J Biol Regul Homeost Agents, (2020), 34(2) 327-331. doi: 10.23812/CONTI-E).

With SARS-CoV- and MERS-CoV-infection, marked inflammatory responses may activate a "cytokine storm", with apoptosis of epithelial and endothelial cells, vascular leakage, and abnormal T cell and macrophage responses (Channappanavar et al., Semin Immunopathol, (2017), 39:529-539). A cytokine storm also may prevail in patients with COVID-19 (Pedersen et al., J Clin Invest, (2020), 1:130(5):2202-2205; Zhang et al., Int J Antimicrob Agents, (2020), 55(5):105954). Dendritic cells and epithelial cells are activated and express a number of pro-inflammatory cytokines and chemokines including interleukin (IL) 1β, IL-2, IL-6, IL-8, interferon (IFN) α/β, tumor necrosis factor (TNF), C-C motif chemokine (CCL) 2, CCL3, CCL5, and interferon-inducible protein (IP) 10. In the blood of patients with COVID-19, there are marked increases in TNF, IFN-γ, IP-10 and CCL2, as well as IL-2, IL-7, IL-10 (Huang et al., Lancet, (2020), 395:497-506). In a multiplex screen for 48 cytokines, Yang et al. reported a marked increase of 14 cytokines (Vaninov et al., Nat Rev Immunol, (2020), 20(5): 277, PMCID: PMC7132547). Excessive inflammation likely contributes importantly to the pathogenesis of COVID-19 (Pedersen et al., J Clin Invest, (2020), 1:130(5):2202-2205; Zhang et al., Int J Antimicrob Agents, (2020), 55(5): 105954).

Evidence is newly emerging that mortality could be as high as two thirds among patients with COVID-19 who are treated with mechanical ventilation (MV), as recently reported from the United Kingdom's Intensive Care National Audit and Research Center, involving 3883 patients with confirmed COVID-1. The finding of worse outcomes with MV may reflect the greater disease burden in patients with hypoxia thought to require MV. Alternatively, higher mortality with MV may reflect, in part, the superimposition of what is termed "ventilator induced lung injury" (VILI) "on top of" the already compromised lung suffering from COVID-19-induced dysfunction. Mechanical ventilation can be lifesaving, but it comes with potential complications (Brower et al., N Engl J Med, (2000), 342:1301-8). Mechanical ventilation itself can activate inflammatory pathways and cause pulmonary edema, i.e., VILI (Parker et al., Crit Care Med, (1993), 21:131-43; Dos Santos et al., J Appl Physiol (1985), (2000), 89:1645-55).

Glibenclamide is a member of the sulfonylurea class of drugs that has been used since the 1960s as an oral hypoglycemic agent for treatment of type II diabetes mellitus (DM) (Marble et al., Drugs, (1971), 1:109-15). In DM, the mechanism of action of glibenclamide involves the inhibition of ATP-sensitive potassium (SUR1-Kir6.2; $K_{ATP}$) channels in pancreatic β cells, resulting in insulin secretion. More recently, an intravenous (IV) formulation of glibenclamide was developed to target sulfonylurea receptor 1—transient receptor potential melastatin 4 (SUR1-TRPM4) channels involved in edema and brain swelling in large strokes and traumatic brain injury (Pergakis et al., Expert Opin Investig Drugs, (2019), 28:1031-1040).

Completely separate from its hypoglycemic and anti-edema effects, a growing body of work has shown that glibenclamide plays an important role in regulating inflammation (see review) (Zhang et al., Mediators Inflamm, (2017), 2017:3578702). Recent research has documented the beneficial effects of SUR1 inhibition by glibenclamide in several proinflammatory conditions involving the central nervous system (CNS) (Simard et al., J Cereb Blood Flow Metab, (2009), 29:317-30; Tosun et al., Stroke, (2013), 44:3522-8; Schattling et al., Nat Med, (2012), 18:1805-11; Makar et al., J Neuroinflammation, (2015), 12:210; Gerzanich et al., J Neuroinflammation, (2017), 14:177; Bianchi, Mol Brain, (2018), 11:41; Abdallah et al., Brain Res, (2011), 1385:257-62; Qu et al., J Neuroinflammation, (2017), 14:228; Esmaeili et al., Behav Brain Res., (2020), 379: 112359). Anti-inflammatory effects of glibenclamide also have been reported in various organs outside the CNS, including the lungs, intestines, pancreas, and kidneys, and in conditions such as melioidosis and cardiac arrest (Pompermayer et al., Kidney Int, (2005), 67:1785-96; Kuipers et al., Anesthesiology, (2012), 116:1104-15; Cui et al., Inflammation (2015), 38:835-45; Liang et al., Toxicol Ind Health, (2017), 33:737-745; Chen et al., Drug Des Devel Ther, (2019), 13:1545-1554; Shao et al., Environ Toxicol, (2020), 35(8):831-839; Pompermayer et al., Eur J Pharmacol, (2007), 556:215-22; York et al., Transl Res, (2014), 164: 259-69; Koh et al., Clin Infect Dis, (2011), 52:717-25; Koh, PLoS Negl Trop Dis, (2013), 7:e2500; Liu et al., PLoS Negl Trop Dis, (2014); 8:e2795; Kewcharoenwong et al., Sci Rep, (2016), 6:34794; Huang et al., Crit Care Med, (2015), 43:e341-9).

In the above contexts, glibenclamide has been shown to reduce NF-κB signaling and to reduce the expression of multiple cytokines, including TNF, IFNγ, IL-1β and IL-18, as well as IL-4, IL-5, IL-6, IL-8, IL-13, IL-17, while it preserves or increases the anti-inflammatory cytokine, IL-10. Glibenclamide also reduces the expression of the chemokines, BAFF, CCL2, CCL17 and CCL27 (Makar et al., J Neuroinflammation, (2015), 12:210; Gerzanich et al., J Neuroinflammation, (2017), 14:177; Abdallah et al., Brain Res, (2011), 1385:257-62; Qu et al., J Neuroinflammation, (2017), 14:228; Esmaeili et al., Behav Brain Res., (2020), 379:112359; Pompermayer et al., Kidney Int, (2005), 67:1785-96; Kuipers et al., Anesthesiology, (2012), 116: 1104-15; Cui et al., Inflammation (2015), 38:835-45; Liang et al., Toxicol Ind Health, (2017), 33:737-745; Chen et al., Drug Des Devel Ther, (2019), 13:1545-1554; Shao et al., Environ Toxicol, (2020), 35(8):831-839; Pompermayer et al., Eur J Pharmacol, (2007), 556:215-22; York et al., Transl Res, (2014), 164:259-69; Liu et al., PLoS Negl Trop Dis, (2014); 8:e2795; Kewcharoenwong et al., Sci Rep, (2016), 6:34794; Huang et al., Crit Care Med, (2015), 43:e341-9; Ling et al., Atherosclerosis, (2013), 226:348-55; Jeong et al., Eur J Pharmacol, (2017), 815:190-201; Dwivedi et al., Naunyn Schmiedebergs Arch Pharmacol, (2020), 393:705-716; Schmid et al., Life Sci. 2011; 89:725-34; Tamura et al., J Pharmacol Sci, (2017), 135:89-95).

The mechanisms for these inhibitory effects of glibenclamide on NF-κB signaling and cytokine/chemokine expression are still under investigation, but may involve the NLRP3 inflammasome or SUR1, either as the SUR1-TRPM4 channel, or as SUR1 in activated neutrophils (Lamkanfi et al., J Cell Biol, (2009), 187:61-70; Su et al., Curr Med Chem, (2021), 28(3):569-582; Woo et al., J Biol Chem, (2013), 288:3655-67). High-dose glibenclamide (EC$_{50}$, 50 μM) in vitro inhibits the NLRP3 inflammasome, independent of SUR1-containing K$_{ATP}$ channels, and high-dose glibenclamide (50-75 mg/kg) in vivo reduces inflammation in various contexts, including lung inflammation (Lamkanfi et al., J Cell Biol, (2009), 187:61-70; Kuipers et al., Anesthesiology, (2012), 116:1104-15; Chen et al., Drug Des Devel Ther, (2019), 13:1545-1554). Conversely, a number of reports have shown that low-dose glibenclamide (EC$_{50}$, 48 nM) in vitro inhibits SUR1-regulated channels, and that low-dose glibenclamide (10 μg/kg) in vivo reduces brain inflammation, (Woo et al., J Biol Chem, (2013), 288:3655-

67; Chen et al., J Neurosci, (2003), 23:8568-77; Simard et al., J Cereb Blood Flow Metab, (2009), 29:317-30; Tosun et al., Stroke, (2013), 44:3522-8; Schattling et al., Nat Med, (2012), 18:1805-11; Makar et al., J Neuroinflammation, (2015), 12:210; Gerzanich et al., J Neuroinflammation, (2017), 14:177; Bianchi, Mol Brain, (2018), 11:41).

To date, the effects of glibenclamide have been reported in three studies on inflammatory acute lung injury, albeit not with ARDS (Kuipers et al., Anesthesiology, (2012), 116: 1104-15; Cui et al., Inflammation (2015), 38:835-45; Chen et al., Drug Des Devel Ther, (2019), 13:1545-1554). In each case, high-dose glibenclamide was used because the authors were specifically targeting the NLRP3 inflammasome, which is 1000-fold less sensitive to glibenclamide than SUR1 (Lamkanfi et al., J Cell Biol, (2009), 187:61-70). The study by Cui et al. involved a murine model of ALI induced by intranasal ovalbumin (OVA) in mice pre-sensitized to OVA (Cui et al., Inflammation (2015), 38:835-45). Glibenclamide (20 mg/kg) significantly reduced the T-helper type 2 (Th2) cytokines, IL-5, IL-4 and IL-13 in bronchioalveolar lavage fluid (BALF). The study by Chen et al. (Chen et al., Drug Des Devel Ther, (2019), 13:1545-1554) involved a rat model of ALI induced by IV administration of oleic acid (OA). Pretreatment with glibenclamide (75 mg/kg IP 1 hour before OA) significantly alleviated pulmonary interstitial edema, infiltration of neutrophils and mononuclear cells, and reduced levels of myeloperoxidase (MPO), a measure of neutrophil abundance, and of malondialdehyde (MDA), a product of ROS lipid peroxidation that is largely attributable to neutrophil activity. The study by Kuipers et al. (Kuipers et al., Anesthesiology, (2012), 116:1104-15) involved a mouse model of ventilator-induced lung injury (VILI) in which mechanical ventilation (MV) was performed using a high tidal volume (V$_T$=15 mL/kg). Glibenclamide (50 mg/kg) reduced pulmonary edema and, in BALF, reduced total protein, neutrophils, IL-1β, IL-6, and keratinocyte-derived chemokine (KC) levels.

The foregoing description of the background is provided to aid in understanding the invention, and is not admitted to be or to describe prior art to the invention.

SUMMARY OF THE INVENTION

It is to be understood that both the foregoing general description of the invention and the following detailed description are exemplary, and thus do not restrict the scope of the invention.

In one aspect, the invention provides a method of treating or preventing lung injury in a subject in need thereof, comprising administering to the subject an effective amount of an agent that inhibits the activity of SUR1.

In another aspect, the invention provides a method of treating or preventing acute lung injury (ALI) in a subject in need thereof, comprising administering to the subject an effective amount of an agent that inhibits the activity of SUR1.

In another aspect, the invention provides a method of treating or preventing acute respiratory distress syndrome (ARDS) in a subject in need thereof, comprising administering to the subject an effective amount of an agent that inhibits the activity of SUR1.

In another aspect, the invention provides a method of treating or preventing ventilator induced lung injury (VILI) in a subject in need thereof, comprising administering to the subject an effective amount of an agent that inhibits the activity of SUR1.

In another aspect, the invention provides a method of treating a coronavirus infection in a subject in need thereof, comprising administering to the subject an effective amount of an agent that inhibits the activity of SUR1.

In another aspect, the invention provides a method of inhibiting MRP8/14 exocytosis from neutrophils in a subject in need thereof, comprising administering to the subject an effective amount of an agent that inhibits the activity of SUR1.

In another aspect, the invention provides a method of treating or preventing lung injury in a subject in need thereof, comprising administering to the subject an effective amount of glibenclamide. In some embodiments, glibenclamide is administered to the subject in an amount of between about 0.5 mg/day to about 10 mg/day.

In another aspect, the invention provides a method of treating or preventing acute lung injury (ALI) in a subject in need thereof, comprising administering to the subject an effective amount of glibenclamide. In some embodiments, glibenclamide is administered to the subject in an amount of between about 0.5 mg/day to about 10 mg/day.

In another aspect, the invention provides a method of treating or preventing acute respiratory distress syndrome (ARDS) in a subject in need thereof, comprising administering to the subject an effective amount of glibenclamide. In some embodiments, glibenclamide is administered to the subject in an amount of between about 0.5 mg/day to about 10 mg/day.

In another aspect, the invention provides a method of treating or preventing ventilator induced lung injury (VILI) in a subject in need thereof, comprising administering to the subject an effective amount of glibenclamide. In some embodiments, glibenclamide is administered to the subject in an amount of between about 0.5 mg/day to about 10 mg/day.

In another aspect, the invention provides a method of treating a coronavirus infection in a subject in need thereof, comprising administering to the subject an effective amount of glibenclamide. In some embodiments, glibenclamide is administered to the subject in an amount of between about 0.5 mg/day to about 10 mg/day.

In another aspect, the invention provides a method of inhibiting MRP8/14 exocytosis from neutrophils in a subject in need thereof, comprising administering to the subject an effective amount of glibenclamide. In some embodiments, glibenclamide is administered to the subject in an amount of between about 0.5 mg/day to about 10 mg/day.

In some embodiments, the administration of the agent reduces inflammation in the lungs. In some embodiments, the administration of the agent reduces pulmonary edema in the lungs. In some embodiments, the administration of the agent reduces neutrophil infiltration into the lungs.

In some embodiments, the SUR1 that is inhibited is contained in a complex. In some embodiments, the SUR1 containing complex comprises a SUR1-TRPM4 channel. In some embodiments, the SUR1 containing complex comprises SUR1 and MRP8/14.

In some embodiments, the subject is infected with a pathogen. In some embodiments, the pathogen is an RNA virus. In some embodiments, the pathogen is a coronavirus. In some embodiments, the coronavirus is selected from the group consisting of severe acute respiratory syndrome coronavirus (SARS-CoV), Middle East respiratory syndrome coronavirus (MERS-CoV) and severe acute respiratory syndrome coronavirus 2 (SARS-CoV-2).

In some embodiments, the agent is a) a SUR1 antagonist; and/or b) a Transient Receptor Potential cation channel subfamily M member 4 (TRPM4) antagonist.

In some embodiments, the SUR1 antagonist is selected from the group consisting of glibenclamide (glyburide), tolbutamide, acetohexamide, chlorpropamide, tolazimide, glipizide, gliquidone, repaglinide, nateglinide, meglitinide, gliclazide, glimepiride, repaglinide, nateglinide, mitiglinide and an active metabolite thereof.

In some embodiments, the SUR1 antagonist is glibenclamide. In some embodiments, glibenclamide is administered to the subject in an amount of between about 0.5 mg/day to about 10 mg/day.

In some embodiments, TRPM4 is selected from the group consisting of flufenamic acid, mefanimic acid, and niflumic acid.

In some embodiments, the agent is administered by intravenous, inhalation (e.g., aerosol mist) subcutaneous, intrathecal, intramuscular, intracutaneous, transcutaneous, intragastric or oral administration.

In some embodiments, the subject is a human. In some embodiments, the subject is on a mechanical ventilator.

In some embodiments, the agent that inhibits the activity of SUR1 is administered as a bolus injection. In some embodiments, the agent that inhibits the activity of SUR1 is administered as an infusion. In some embodiments, the agent that inhibits the activity of SUR1 is administered as a bolus injection in combination with an infusion. In some embodiments, the agent that inhibits the activity of SUR1 is administered as a loading dose followed by a constant infusion.

In another aspect, the invention provides a method of screening for agents that inhibit MRP8/14 exocytosis from a cell, comprising i) providing a cell expressing MRP8/14 and SUR1 or functional equivalents thereof; ii) contacting the cell with an agent that potentially inhibits the activity of SUR1; and iii) assaying for the exocytosis of MRP8/14 from the cell. In some embodiments, the method further comprises comparing the exocytosis of MRP8/14 from the cell with exocytosis of MRP8/14 from cells that have not been treated with the agent. In some embodiments, the cells are immune cells such as neutrophil cells. In some embodiments, the cells express MRP8/14 and SUR1 endogenously. In some embodiments, the cells have been transfected or engineered to express MRP8/14 and/or SUR1.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The skilled artisan will understand that the drawings, described below, are for illustration purposes only. The drawings are not intended to limit the scope of the present teachings in any way.

FIG. 1. Mechanical ventilation (MV) induces upregulation of SUR1 and TRPM4 in lung alveolae. Immunolabeling for SUR1 (red) and TRPM4 (green) in the lungs of a naïve, non-ventilated rat (naïve, left column) and of a rat that underwent mechanical ventilation for 4 hours and was euthanized 24 hours later (ventilation, right column). The bar graphs show quantification (mean±SE) of the immuno-labeling data for alveolar SUR1 and TRPM4. Tidal volume, 10 mL/kg. ROI=region of interest.

DETAILED DESCRIPTION OF THE INVENTION

Figure 2:
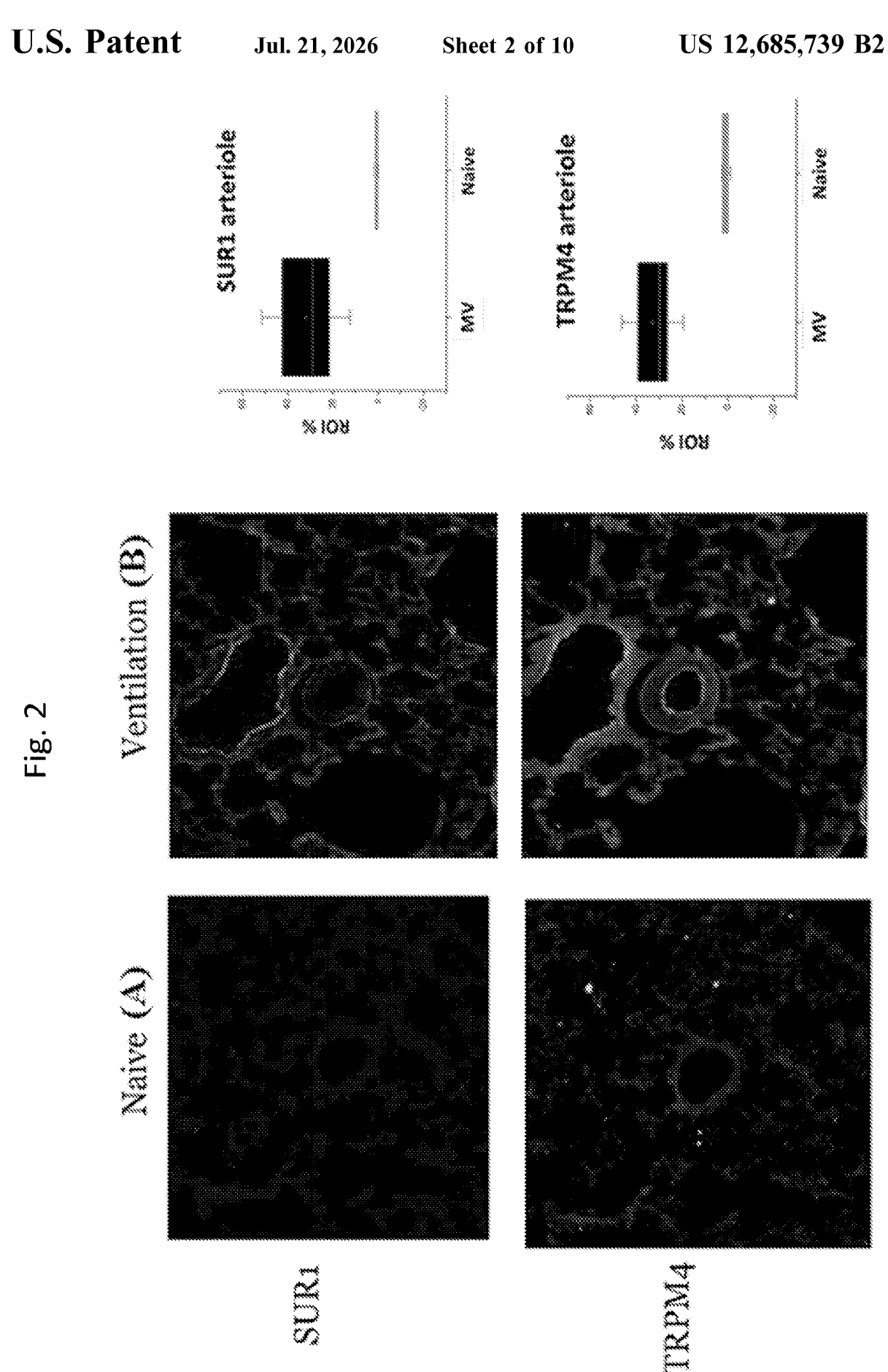
FIG. 2. Mechanical ventilation (MV) induces upregulation of SUR1 and TRPM4 in lung arterioles. Immunolabeling for SUR1 (red) and TRPM4 (green) in the lungs of a naïve, non-ventilated rat (naïve, left column) and of a rat that underwent mechanical ventilation for 4 hours and was euthanized 24 hours later (ventilation, right column). The bar graphs show quantification (mean±SE) of the immuno-labeling data for arteriolar SUR1 and TRPM4. Tidal volume, 10 mL/kg.

Reference will now be made in detail to embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. Furthermore, where the description of one or more embodiments uses the term "comprising," those skilled in the art would understand that, in some specific instances, the embodiment or embodiments can be alternatively described using the language "consisting essentially of" and/or "consisting of." As used herein, the term "about" means at most plus or minus 10% of the numerical value of the number with which it is being used.

It is contemplated that any method or composition described herein can be implemented with respect to any other method or composition described herein.

One skilled in the art may refer to general reference texts for detailed descriptions of known techniques discussed herein or equivalent techniques. These texts include *Current Protocols in Molecular Biology* (Ausubel et. al., eds. John Wiley & Sons, N.Y. and supplements thereto), *Current Protocols in Immunology* (Coligan et al., eds., John Wiley St Sons, N.Y. and supplements thereto), *Current Protocols in Pharmacology* (Enna et al., eds. John Wiley & Sons, N.Y. and supplements thereto) and *Remington: The Science and Practice of Pharmacy* (Lippincott Williams & Wilicins, 2Vt edition (2005)), for example.

Therapeutic Methods

In one embodiment, the invention provides a method of treating or preventing lung injury in a subject in need thereof, comprising administering to the subject an effective amount of an agent that inhibits the activity of SUR1.

In another embodiment, the invention provides a method of treating or preventing acute lung injury (ALI) in a subject in need thereof, comprising administering to the subject an effective amount of an agent that inhibits the activity of SUR1.

In another embodiment, the invention provides a method of treating or preventing acute respiratory distress syndrome (ARDS) in a subject in need thereof, comprising administering to the subject an effective amount of an agent that inhibits the activity of SUR1.

In another embodiment, the invention provides a method of treating or preventing ventilator induced lung injury (VILI) in a subject in need thereof, comprising administering to the subject an effective amount of an agent that inhibits the activity of SUR1.

In another embodiment, the invention provides a method of treating a coronavirus infection in a subject in need thereof, comprising administering to the subject an effective amount of an agent that inhibits the activity of SUR1.

In another embodiment, the invention provides a method of inhibiting MRP8/14 exocytosis from neutrophils in a subject in need thereof, comprising administering to the subject an effective amount of an agent that inhibits the activity of SUR1.

In another embodiment, the invention provides a method of treating or preventing lung injury in a subject in need thereof, comprising administering to the subject an effective amount of glibenclamide.

In another embodiment, the invention provides a method of treating or preventing acute lung injury (ALI) in a subject in need thereof, comprising administering to the subject an effective amount of glibenclamide.

In another embodiment, the invention provides a method of treating or preventing acute respiratory distress syndrome (ARDS) in a subject in need thereof, comprising administering to the subject an effective amount of glibenclamide.

In another embodiment, the invention provides a method of treating or preventing ventilator induced lung injury (VILI) in a subject in need thereof, comprising administering to the subject an effective amount of glibenclamide.

In another embodiment, the invention provides a method of treating a coronavirus infection in a subject in need thereof, comprising administering to the subject an effective amount of glibenclamide.

In another aspect, the invention provides a method of inhibiting MRP8/14 exocytosis from neutrophils in a subject in need thereof, comprising administering to the subject an effective amount of glibenclamide.

In some embodiments, the administration of the agent such as glibenclamide reduces inflammation in the lungs. In some embodiments, the administration of the agent reduces pulmonary edema in the lungs. In some embodiments, the administration of the agent reduces neutrophil infiltration into the lungs.

During lung injury, an inflammatory response can trigger neutrophil adhesion to endothelium and transmigration to tissue and subsequent neutrophil-mediated endothelial and tissue injury.

In some embodiments, the subject to be treated has an inflammatory lung disease or is at risk of having such a disease, and thereby treating or preventing lung injury. An inflammatory lung disease refers to a disease associated with an inflammatory or immune response in the lung. Inflammatory lung diseases include, for example, ALI, ARDS, asthma, emphysema, chronic bronchitis, cystic fibrosis, infection, physical trauma, hemorrhage and interstitial lung disease such as interstitial pneumonitis, idiopathic fibrosis and interstitial fibrosis.

Treating an inflammatory lung disease is intended to refer to the alleviation of a sign or symptom of the inflammatory lung disease. Treating an inflammatory lung disease is intended to encompass a reduction in the onset or magnitude of a sign or symptom of an inflammatory lung disease, such as the recruitment of neutrophils.

Acute lung injury (ALI) and its more severe presentation, the Acute Respiratory Distress Syndrome (ARDS), are important causes of morbidity and mortality. ARDS is a type of respiratory failure characterized by the rapid onset of widespread inflammation and edema in the lungs (Fan et al., JAMA, (2018), 319(7):698-710). Symptoms include shortness of breath, rapid breathing, and bluish skin discoloration due to hypoxia (Fan et al., JAMA, (2018), 319(7):698-710). Acute lung injury and ARDS mark the advanced stages of numerous respiratory diseases, including chemical lung injuries, bacterial infections and viral infections.

ALI occurs when an insult to the lung causes an acute inflammatory reaction which results in respiratory distress, hypoxemia and diffuse alveolar infiltrates, and can ultimately lead to respiratory failure. ALI can be induced by a variety of causes. In certain aspects, the ALI can be induced by inhalation or aspiration of a chemical irritant, pneumonia, sepsis, trauma, aspiration of gastric contents, blood transfusions, drug overdose, pancreatitis, burns, near drowning, pulmonary embolus, reperfusion injury, or a combination thereof.

The extent of ALI depends, for example, on the magnitude of initial damage, repeated insults such as persistent septicemia or retained necrotic and inflamed tissue, and added insults from treatment including barotrauma, hyperoxia and nosocomial infection.

ALI that is induced by inhalation or aspiration of a chemical irritant can be inducted by a variety of chemical irritants. Examples of chemical irritants that can induce ALI that is responsive to the methods and compositions described herein include, but are not limited to, chlorine gas, smoke, phosgene, hydrochloric acid, Acrolein, Ammonia, Aniline, Arsenic trioxide, Arsine, Boron trifluoride, Cyanogen chloride, Hydrogen fluoride, Hydrogen sulfide, Methyl isocyanate, Phosphoro trichloride, Phosphorus trichloride, Sulfur dioxide, Sulfur trioxide, Chlorine dioxide, Bromine, Epichlorohydrin, Fluorine, Hydrazine, Hydrogen selenide, Methyl hydrazine, Benzenethiol, Dimethyl sulfate, Perfluoroisobutene, and combinations thereof.

ARDS is a form of acute lung injury often seen in previously healthy patients. ARDS is characterized by rapid respiratory rates, a sensation of profound shortness of breath, severe hypoxemia not responsive to supplemental oxygen, and widespread pulmonary infiltrates by cardiovascular disease or volume overload. ARDS tends to follow a diverse array of systemic and pulmonary insults, although the majority of ARDS is associated with systemic or pulmonary infection, severe trauma, or aspirating gastric contents. The crucial stimulus to the development of ARDS is an inflammatory response to distant or local tissue injury. Disorders associated with ARDS include aspiration of gastric contents, fresh and salt water and hydrocarbons; central nervous system trauma, anoxia, seizures or increased intracranial pressure; drug overdose or reactions; hematologic alterations; infection, including sepsis, pneumonia and tuberculosis; inhalation of toxins such as oxygen, smoke or corrosive chemicals; metabolic disorders such as pancreatitis; shock; and trauma such as fat emboli, lung contusion, severe nonthoracic trauma and cardiopulmonary bypass.

Ventilator induced lung injury (VILI) is caused by distension of lung tissues. Stretch forces can cause activation of the p38 MAPK pathway and the mechanosensitive transcription factor, NF-kappaB, resulting in the release of numerous pro-inflammatory cytokines, including IL-6, IL-8, IL-1beta, and TNFalpha (Dos Santos et al., J Appl Physiol (1985), (2000), 89(4):1645-55; Ricard et al., Eur Respir J Suppl, (2003), 42:2s-9s; Liu et al., Transl Res, (2009), 154(5):228-40; Lionetti et al., Curr Opin Crit Care, (2005), 11(1):82-6; Birukova et al., Am J Pathol, (2006), 168(5):1749-61). This pro-inflammatory milieu leads to the leakage of pulmonary edema fluid into the lung tissue, resulting in impaired gas exchange and poor oxygenation. Stretch forces also generate reactive oxygen species, which further exacerbate VILI (Davidovich et al., Am J Respir Cell Mol Biol, (2013), 49(1):156-64).

In some embodiments of the method as described herein, the subject is administered an effective amount of an agent that inhibits the activity of SUR1.

In some embodiments, the agent reduces the amount or expression of pro-inflammatory cytokines in lung tissue. In some embodiments, the pro-inflammatory cytokines are selected from IL-6, MCP-1, IL-8, IL-1beta, TNFalpha and combinations thereof. In some embodiments, the cytokines are IL-6 and MCP-1.

In some embodiments, the SUR1 that is inhibited is contained in a complex. In some embodiments, the SUR1 containing complex comprises a SUR1-TRPM4 channel. In some embodiments, the SUR1 containing complex comprises SUR1 and MRP8/14.

The Sur1-Trpm4 channel is a $NC_{Ca-ATP}$ channel. As used herein, the term "$NC_{Ca-ATP}$ channel" refers to a non-selective cation channel complex that is activated by intracellular calcium and blocked by intracellular ATP, and has a single-channel conductance to potassium ion ($K^+$) of between about 20 and about 50 pS at physiological potassium concentrations. This channel complex includes a SUR1 receptor and is sensitive to SUR1 agonists and antagonists. In certain embodiments, the channel complex includes a pore that has similar properties to the TRPM4 channels, including blockade by TRPM4 blockers (such as, e.g., flufenamic acid, mefanimic acid, and niflumic acid), and therefore the pore of the $NC_{Ca-ATP}$ channel complex is TRPM4 channel. This channel complex is referred to herein as a "channel" and is described in greater detail elsewhere in the application.

As used herein, the term "TRPM4 channel" refers to a pore that passed ions that is a member of the transient receptor potential channel family (hence the acronym "TRP") and is the pore forming portion of the SUR1-sensitive $NC_{Ca-ATP}$ channel.

As used herein, the terms "agent that inhibits the activity" refers to a biological or chemical agent that acts within the body to reduce the physiological activity of another chemical or biological substance. In the present invention, the agent blocks, inhibits, reduces and/or decreases the activity of SUR1, such as a SUR1 containing complex of a cell, such as a neutrophil. In some embodiments of the invention, without being bound by theory, the agent combines, binds, associates with a Sur1-Trpm4 channel cell such that the channel is closed (deactivated), meaning reduced biological activity with respect to the biological activity in the diseased state. In certain embodiments, without being bound by theory, the agent combines, binds and/or associates with a Sur1-MRP8/14 complex and inhibits exocytosis of MRP8/14 from an immune cell, such as a neutrophil. In some embodiments, the antagonist combines, binds, and/or associates with a pore-forming subunit of the Sur1-Trpm4 channel, such that the channel is closed (deactivated). The terms antagonist, agent or inhibitor can be used interchangeably.

As used herein, the terms "effective amount" or "therapeutically effective amount" are interchangeable and refer to an amount that results in an improvement or remediation of at least one symptom of the disease or condition. Those of skill in the art understand that the effective amount may improve the patient's or subject's condition, but may not be a complete cure of the disease and/or condition.

As used herein, the term "inhibit" refers to the ability of the compound to block, partially block, interfere, decrease, reduce or deactivate a process. molecule or complex, such as a channel (e.g., a Sur1-Trpm4 channel). Thus, one of skill in the art understands that the term inhibit can encompass a complete and/or partial loss of activity of a channel, such as the Sur1-Trpm4 channel. Channel activity may be inhibited by channel block (occlusion or closure of the pore region, preventing ionic current flow through the channel), by changes in an opening rate or in the mean open time, changes in a closing rate or in the mean closed time, or by other means. For example, a complete and/or partial loss of activity of the Sur1-Trpm4 channel as may be indicated by a reduction in cell depolarization, reduction in sodium ion influx or any other monovalent ion influx, reduction in an influx of water, reduction in extravasation of blood, reduction in cell death, as well as an improvement in cellular survival following an ischemic challenge.

The term "preventing" as used herein refers to minimizing, reducing or suppressing the risk of developing a disease state or parameters relating to the disease state or progression or other abnormal or deleterious conditions.

The terms "treating" and "treatment" as used herein refer to administering to a subject a therapeutically effective amount of an agent so that the subject has an improvement in the disease or condition. The improvement is any observable or measurable improvement. Thus, one of skill in the art realizes that a treatment may improve the patient's condition, but may not be a complete cure of the disease. Treating may also comprise treating subjects at risk of developing a disease and/or condition.

The $NC_{Ca-ATP}$ channel is distinguished by certain functional characteristics, the combination of which distinguishes it from other ion channels. The characteristics that distinguish the $NC_{Ca-ATP}$ channel include, but are not necessarily limited to, the following: 1) it is a non-selective cation channel that readily allows passage of Na, K, and other monovalent cations; 2) it is activated by an increase in intracellular calcium, and/or by a decrease in intracellular ATP; 3) it is regulated by sulfonylurea receptor type 1 (SUR1, which previously had been considered to be associated exclusively with $K_{ATP}$ channels such as those found in pancreatic β-cells, for example.

The $NC_{Ca-ATP}$ channel was identified first in native reactive astrocytes (NRAs) and later in neurons and capillary endothelial cells after stroke or traumatic brain or spinal cord injury (see at least International Application WO 03/079987 which is incorporated by reference herein in its entirety). As with the $K_{ATP}$ channel in pancreatic β-cells, the $NC_{Ca-ATP}$ channel is considered to be a heteromultimer structure comprised of sulfonylurea receptor type 1 (SUR1) regulatory subunits and pore-forming subunits. The pore-forming subunits have been characterized biophysically and have been identified as TRPM4.

More specifically, the $NC_{Ca-ATP}$ channel has a single-channel conductance to potassium ion ($K^+$) between 20 and 50 pS. The $NC_{Ca-ATP}$ channel is also stimulated by $Ca^{2+}$ on the cytoplasmic side of the cell membrane in a physiological concentration range, where said concentration range is from $10^{-8}$ to $10^{-5}$ M. The $NC_{Ca-ATP}$ channel is also inhibited by cytoplasmic ATP in a physiological concentration range, where said concentration range is from about $10^{-1}$ to about 5 mM. The $NC_{Ca-ATP}$ channel is also permeable to the following cations; $K^+$, $Cs^+$, $Li^+$, $Na^+$; to the extent that the permeability ratio between any two of said cations is greater than 0.5 and less than 2. The $NC_{Ca-ATP}$ channel is disclosed in U.S. Pat. No. 9,375,438, which is herein incorporated by reference in its entirety.

In some embodiments, the agent that inhibits the activity of SUR1 is an inhibitor of a Sur1-Trpm4 channel. In some embodiments, the agent is a) a SUR1 antagonist; and/or b) a Transient Receptor Potential cation channel subfamily M member 4 (TRPM4) antagonist.

In one aspect, the SUR1-TRPM4 channel is blocked, inhibited, or otherwise is decreased in activity. In such examples, an antagonist of the SUR1-TRPM4 channel is administered and/or applied. In some embodiments, the antagonist modulates the SUR1-TRPM4 channel such that flux through the channel is reduced, ceased, decreased and/or stopped. The antagonist may have a reversible or an irreversible activity with respect to the activity of the Sur1-Trpm4 channel of a cell. The antagonist may prevent or lessen the depolarization of the cells thereby lessening cell swelling due to osmotic changes that can result from depolarization of the cells.

Inhibitors of SUR1 can include such compounds as glibenclamide (glyburide), tolbutamide, repaglinide, nateglinide, meglitinide, chlorpropamide, tolazimide, glipizide, gliquidone, repaglinide, nateglinide, mitiglinide, iptakalim, endosulfines, LY397364, LY389382, gliclazide, glimepiride, MgADP, endosulfines, estrogen, estrogen related-compounds including estradiol, estrone, estriol, genistein, non-steroidal estrogen (e.g., diethylstilbestrol), phytoestrogen (e.g., coumestrol), zearalenone, etc., and combinations thereof. Examples of antagonists may encompass respective antagonists identified in U.S. Patent Application Publication No. 2003/0215889, which is incorporated herein by reference in its entirety.

Subjects that can be treated with the therapeutic compositions of the present invention can include subjects with lung injury, ALI, ARDS, COVID-19, or subjects who are at risk thereof. The term "subject" refers to any animal (e.g., a mammal), including, but not limited to humans, non-human primates, rodents, pets, such as dogs, cats, horses, etc., agricultural animals such as cows, sheep, goats and the like, which is to be the recipient of a particular treatment. Typically, the terms "subject" and "patient" are used interchangeably herein in reference to a human subject.

In some embodiments, the subject is infected with a pathogen. In some embodiments, the pathogen is an RNA virus. In some embodiments, the pathogen is a coronavirus. In some embodiments, the coronavirus is selected from the group consisting of severe acute respiratory syndrome coronavirus (SARS-CoV), Middle East respiratory syndrome coronavirus (MERS-CoV) and severe acute respiratory syndrome coronavirus 2 (SARS-CoV-2).

In some embodiments, the subject is on a mechanical ventilator. In some embodiments, the subject is hypoxic or having difficulty breathing, but is not yet on a ventilator.

In some embodiments, the SUR1 inhibitor is glibenclamide. In some embodiments, glibenclamide is administered to the subject, such as a human, in an amount of between about 0.5 mg/day to about 10 mg/day. In some embodiments, glibenclamide is administered to the subject, such as a human, in an amount of between about 1.0 mg/day to about 10 mg/day, about 1.0 mg/day to about 7.5 mg/day, about 1.0 mg/day to about 5.0 mg/day, about 1.0 mg/day to about 3.0 mg/day, about 2.0 mg/day to about 4.0 mg/day, about 2.5 mg/day to about 3.5 mg/day, or from about 2.75 mg/day to about 3.25 mg/day. In some embodiments, glibenclamide is administered to the subject, such as a human, in an amount of about 3.0 mg/day.

In some embodiments, the agent that is administered is a TRPM4 antagonist. In some embodiments, the TRPM4 antagonist is selected from the group consisting of flufenamic acid, mefanimic acid, and niflumic acid.

In some embodiments, an effective amount of the inhibitor of the SUR1-TRPM4 channel that is administered includes a dose of about 0.0001 nM to about 2000 μM. In some embodiments, amount administered is from about 0.01 nM to about 2000 μM; about 0.01 μM to about 0.05 μM; about 0.05 μM to about 1.0 μM; about 1.0 μM to about 1.5 μM; about 1.5 μM to about 2.0 μM; about 2.0 μM to about 3.0 μM; about 3.0 μM to about 4.0 μM; about 4.0 μM to about 5.0 μM; about 5.0 μM to about 10 μM; about 10 μM to about 50 μM; about 50 μM to about 100 μM; about 100 μM to about 200 μM; about 200 μM to about 300 μM; about 300 μM to about 500 μM; about 500 μM to about 1000 μM; about 1000 μM to about 1500 μM; and about 1500 μM to about 2000 μM. Of course, all of these amounts are exemplary, and any amount in-between these points is also expected to be of use in the invention.

In some embodiments, the invention provides a composition for treating or preventing lung injury in a subject, comprising an effective amount of an agent that inhibits SUR1 as provided herein and a pharmaceutically acceptable carrier.

In some embodiments, the inhibitor can be administered parenterally or alimentarily. Parenteral administrations include, but are not limited to intravenously, intradermally, inhalation, transdermally, intramuscularly, intraarterially, intrathecally, subcutaneous, or intraperitoneally. See, e.g., U.S. Pat. Nos. 6,613,308, 5,466,468, 5,543,158; 5,641,515; and 5,399,363 (each specifically incorporated herein by reference in its entirety). Alimentary administrations include, but are not limited to orally, buccally, rectally, or sublingually.

In some embodiments, the administration of the therapeutic compounds and/or the therapies of the present invention may include systemic, local and/or regional administrations, for example, topically (dermally, transdermally), via catheters, implantable pumps, dermal patches, transdermal patches, etc. Alternatively, other routes of administration are also contemplated such as, for example, arterial perfusion, intracavitary, intraperitoneal, intrapleural, inhalation (e.g., aerosol or mist), intramuscular, intraventricular and/or intrathecal. The skilled artisan is aware of determining the appropriate administration route using standard methods and procedures. Other routes of administration are discussed elsewhere in the specification and are incorporated herein by reference.

Treatment methods involve treating an individual with an effective amount of a composition containing a therapeutically active agent. An effective amount is described, generally, as that amount sufficient to detectably and repeatedly to ameliorate, reduce, minimize or limit the extent of a disease or its symptoms.

As is well known in the art, a specific dose level of active compounds for any particular patient depends upon a variety of factors including the activity of the specific compound employed, the age, body weight, general health, sex, diet, time of administration, route of administration, rate of excretion, drug combination, and the severity of the particular disease undergoing therapy.

In some embodiments, the compound(s) or composition(s) can be administered to the subject once, such as by a single injection or deposition at or near the site of interest. In some embodiments, the compound(s) or composition(s) can be administered to a subject over a period of days, weeks, or months. In some embodiments, the compound(s) or composition(s) is administered at least once a day to a subject. Where a dosage regimen comprises multiple administrations, it is understood that the effective amount of the compound(s) or composition(s) administered to the subject can comprise the total amount of the compound(s) or composition(s) administered over the entire dosage regimen.

In some embodiments, the agent can comprise a compound (protein, nucleic acid, siRNA, etc.) that modulates transcription and/or translation of SUR1 (regulatory subunit), TRPM4, and/or the molecular entities that comprise the pore-forming subunit.

Transcription factors are regulatory proteins that binds to a specific DNA sequence (e.g., promoters and enhancers) and regulate transcription of an encoding DNA region. Thus, transcription factors can be used to modulate the expression of SUR1. Typically, a transcription factor comprises a binding domain that binds to DNA (a DNA-binding domain) and a regulatory domain that controls transcription. Where a regulatory domain activates transcription, that regulatory domain is designated an activation domain. Where that regulatory domain inhibits transcription, that regulatory domain is designated a repression domain. More specifically, transcription factors such as Sp1, HIF1, and NFkappaB can be used to modulate expression of SUR1.

In some embodiments, a transcription factor may be targeted by a composition of the invention. The transcription factor may be one that is associated with a pathway in which SUR1 is involved. The transcription factor may be targeted with an antagonist of the invention, including siRNA to downregulate the transcription factor. Such antagonists can be identified by standard methods in the art, and in particular embodiments the antagonist is employed for treatment and or prevention of an individual in need thereof. In an additional embodiment, the antagonist is employed in conjunction with an additional compound, such as a composition that modulates the SUR1-TRPM4 channel of the invention. For example, the antagonist may be used in combination with an inhibitor of the channel of the invention. When employed in combination, the antagonist of a transcription factor of a SUR1-related pathway may be administered prior to, during, and/or subsequent to the additional compound.

An antisense molecule that binds to a translational or transcriptional start site, or splice junctions, are ideal inhibitors. Antisense, ribozyme, and double-stranded RNA molecules target a particular sequence to achieve a reduction or elimination of a particular polypeptide, such as SUR1. Thus, it is contemplated that antisense, ribozyme, and double-stranded RNA, and RNA interference molecules are constructed and used to modulate SUR1 expression.

Antisense methodology takes advantage of the fact that nucleic acids tend to pair with complementary sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases, such as inosine, 5-methylcytosine, 6-methyladenine, hypoxanthine and others, in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNAs, are employed to inhibit gene transcription or translation or both within a host cell, either in vitro or in vivo, such as within a host animal, including a human subject.

Antisense constructs are designed to bind to the promoter and other control regions, exons, introns or even exon-intron boundaries of a gene. It is contemplated that the most effective antisense constructs may include regions complementary to intron/exon splice junctions. Thus, in some embodiments, antisense constructs with complementarity to regions within 50-200 bases of an intron-exon splice junction are used. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

It is advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

It is also contemplated in the present invention that double-stranded RNA is used as an interference molecule, e.g., RNA interference (RNAi). In some embodiments, RNA interference is used to "knock down" or inhibit a particular gene of interest by simply injecting, bathing or feeding to the organism of interest the double-stranded RNA molecule. This technique selectively "knock downs" gene function without requiring transfection or recombinant techniques.

Another type of RNAi is often referred to as small interfering RNA (siRNA), which may also be utilized to inhibit SUR1. A siRNA may comprise a double stranded structure or a single stranded structure, the sequence of which is "substantially identical" to at least a portion of the target gene (see WO 04/046320, which is incorporated herein by reference in its entirety). "Identity," as known in the art, is the relationship between two or more polynucleotide (or polypeptide) sequences, as determined by comparing the sequences. In the art, identity also means the degree of sequence relatedness between polynucleotide sequences, as determined by the match of the order of nucleotides between such sequences. Identity can be readily calculated. See, for example: Computational Molecular Biology, Lesk, A. M., ed. Oxford University Press, New York, 1988; Biocomputing: Informatics and Genome Projects, Smith, D. W., ea., Academic Press, New York, 1993, and the methods disclosed in WO 99/32619, WO 01/68836, WO 00/44914, and WO 01/36646, specifically incorporated herein by reference. While a number of methods exist for measuring identity between two nucleotide sequences, the term is well known in the art. Methods for determining identity are typically designed to produce the greatest degree of matching of nucleotide sequence and are also typically embodied in computer programs. Such programs are readily available to those in the relevant art. For example, the GCG program package (Devereux et al.), BLASTP, BLASTN, and FASTA and CLUSTAL.

Thus, siRNA contains a nucleotide sequence that is essentially identical to at least a portion of the target gene, for example, SUR1, or any other molecular entity associated with the NC$_{Ca-ATP}$ channel such as the pore-forming subunit. One of skill in the art is aware that the nucleic acid sequences for SUR1 are readily available in GenBank, for example, GenBank accession L40624, which is incorporated herein by reference in its entirety. Preferably, the siRNA contains a nucleotide sequence that is completely identical to at least a portion of the target gene. Of course, when comparing an RNA sequence to a DNA sequence, an "identical" RNA sequence will contain ribonucleotides where the DNA sequence contains deoxyribonucleotides, and further that the RNA sequence will typically contain a uracil at positions where the DNA sequence contains thymidine.

One of skill in the art will appreciate that two polynucleotides of different lengths may be compared over the entire length of the longer fragment. Alternatively, small regions may be compared. Normally sequences of the same length are compared for a final estimation of their utility in the practice of the present invention. It is preferred that there be 100% sequence identity between the dsRNA for use as siRNA and at least 15 contiguous nucleotides of the target gene (e.g., SUR1), although a dsRNA having 70%, 75%, 80%, 85%, 90%, or 95% or greater may also be used in the present invention. A siRNA that is essentially identical to a least a portion of the target gene may also be a dsRNA wherein one of the two complementary strands (or, in the case of a self-complementary RNA, one of the two self-complementary portions) is either identical to the sequence of that portion or the target gene or contains one or more insertions, deletions or single point mutations relative to the nucleotide sequence of that portion of the target gene. siRNA technology thus has the property of being able to tolerate sequence variations that might be expected to result from genetic mutation, strain polymorphism, or evolutionary divergence.

There are several methods for preparing siRNA, such as chemical synthesis, in vitro transcription, siRNA expression vectors, and PCR expression cassettes. Irrespective of which method one uses, the first step in designing an siRNA molecule is to choose the siRNA target site, which can be any site in the target gene. In certain embodiments, one of skill in the art may manually select the target selecting region of the gene, which may be an ORF (open reading frame) as the target selecting region and may preferably be 50-100 nucleotides downstream of the "ATG" start codon. However, there are several readily available programs available to assist with the design of siRNA molecules, for example siRNA Target Designer by Promega, siRNA Target Finder by GenScript Corp., siRNA Retriever Program by Imgenex Corp., EMBOSS siRNA algorithm, siRNA program by Qiagen, Ambion siRNA predictor, Ambion siRNA predictor, Whitehead siRNA prediction, and Sfold. Thus, it is envisioned that any of the above programs may be utilized to produce siRNA molecules that can be used in the present invention.

Ribozymes are RNA-protein complexes that cleave nucleic acids in a site-specific fashion. Ribozymes have specific catalytic domains that possess endonuclease activity. For example, a large number of ribozymes accelerate phosphoester transfer reactions with a high degree of specificity, often cleaving only one of several phosphoesters in an oligonucleotide substrate. This specificity has been attributed to the requirement that the substrate bind via specific base-pairing interactions to the internal guide sequence ("IGS") of the ribozyme prior to chemical reaction. Ribozyme catalysis has primarily been observed as part of sequence specific cleavage/ligation reactions involving nucleic acids. For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression is particularly suited to the therapeutic applications. Most of this work involved the modification of a target mRNA, based on a specific mutant codon that is cleaved by a specific ribozyme. In light of the information included herein and the knowledge of one of ordinary skill in the art, the preparation and use of additional ribozymes that are specifically targeted to a given gene will now be straightforward.

Designing and testing ribozymes for efficient cleavage of a target RNA is a process well known to those skilled in the art. The identification of operative and preferred sequences for use in SUR1 targeted ribozymes is simply a matter of preparing and testing a given sequence, and is a routinely practiced screening method known to those of skill in the art.

Following expression of individual regulatory and pore-forming subunit proteins of the channel, and in particular aspects of the invention, these proteins are modified by glycosylation in the Golgi apparatus of the cell, assembled into functional heteromultimers that comprise the channel, and then transported to the plasmalemmal membrane where they are inserted to form functional channels. The last of these processes is referred to as "trafficking."

In specific embodiments of the invention, molecules that bind to any of the constituent proteins interfere with post-translational assembly and trafficking, and thereby interfere with expression of functional channels. One such example is with glibenclamide binding to SUR1 subunits. In additional embodiments, glibenclamide, which binds with femtomolar affinity to SUR1, interferes with post-translational assembly and trafficking required for functional channel expression.

Screening Assays

In another embodiment, the invention provides a method of screening for agents that inhibit MRP8/14 exocytosis from a cell, comprising i) providing a cell expressing MRP8/14 and SUR1 or functional equivalents thereof; ii) contacting the cell with an agent that potentially inhibits the activity of SUR1; and iii) assaying for the exocytosis of MRP8/14 from the cell. In some embodiments, the method further comprises comprising comparing the exocytosis of MRP8/14 from the cell with exocytosis of MRP8/14 from cells that have not been treated with the agent.

In some embodiments, the screening procedures involve producing appropriate cells, which can be neutrophil cells, that express MRP8/14 and SUR1 or functional equivalents thereof. The cells are not particularly limiting. In some embodiments, the cells are immune cells. In some embodiments, the cells are neutrophil cells.

Such cells can include cells from mammals, yeast, *Drosophila* or *E. coli*. In some embodiments, the cells express the polypeptide(s) endogenously. In other embodiments, the cells have been transfected or engineered to express the polypeptide. In some embodiments, cells expressing the protein(s) (or extracts or purified preparations from cells) are contacted with a test compound to observe stimulation or inhibition of a functional response.

In some embodiments, for assaying agents that inhibit expression of SUR1, the levels of SUR1 mRNA or protein can be assayed after contacting the cells with the test compound. In some embodiments, the expression level of an endogenous SUR1 target gene is assayed. In some embodiments, the cells can comprise a reporter gene located downstream of one or more SUR1 promoter elements and inhibition of the reporter gene is assayed.

Examples of inhibitors can include antibodies, peptides, carbohydrates, nucleic acids, lipids, or small molecules. These agents can be selected and screened 1) at random, 2) by a rational selection or 3) by design using for example, protein or ligand modeling techniques (preferably, computer modeling).

Combination Therapy

The active agents of the present invention can be administered alone or in combination with one or more additional active pharmaceutical agents. In some embodiments, the active agents of the invention are administered with one or more additional active pharmaceutical agents that are useful to treat lung injury, ALI, ARDS, or an infection such as a coronavirus infection.

In some embodiments, such additional pharmaceutical agents can include one or more corticosteroids, exogenous surfactants, statins, beta-blockers, n-acetylcysteine, anti-inflammatory agents, immunosuppressants, therapeutic antibodies, antibiotics, or antiviral agents.

In one embodiment, the additional pharmaceutical agent is remdesivir or an analogue thereof.

In one embodiment, the additional pharmaceutical agent is one or more of the compounds disclosed by Wu et al., "Analysis of therapeutic targets for SARS-CoV-2 and discovery of potential drugs by computational methods," *Acta Pharmaceutica Sinica B* https://doi.org/10.1016/j.apsb.2200.02.008 which is incorporated by reference herein.

In some embodiments, the additional pharmaceutically active agent comprises one or more anti-SARS-CoV-2 antibodies. In some embodiments, the antibody is a monoclonal antibody. In some embodiments, the antibodies are polyclonal antibodies, such as those obtained from convalescent serum of recovered patients. In some embodiments, the antibody targets the spike protein. In some embodiments, the antibody targets the receptor binding domain (RBD) of the SARS-CoV-2 spike protein. The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments, dual affinity retargeting antibodies (DART)), single chain Fv (scFv) mutants, multispecific antibodies such as bispecific and trispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity.

The combined administration includes co-administration, using separate formulations or a single pharmaceutical formulation, and consecutive administration in either order, wherein preferably there is a time period while both (or all) active agents simultaneously exert their biological activities.

Single or multiple administrations of the compositions that are disclosed herein can be administered depending on the dosage and frequency as required and tolerated by the patient. The dosage can be administered once, but may be applied periodically until either a therapeutic result is achieved or until side effects warrant discontinuation of therapy.

Compositions

The present invention also contemplates therapeutic methods employing compositions comprising the active substances disclosed herein. Preferably, these compositions include pharmaceutical compositions comprising a therapeutically effective amount of one or more of the active compounds or substances along with a pharmaceutically acceptable carrier.

As used herein, the term "pharmaceutically acceptable" carrier means a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate;

powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations.

Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically acceptable antioxidants include, but are not limited to, water soluble antioxidants such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, alpha-tocopherol and the like; and the metal chelating agents such as citric acid, ethylenediamine tetraacetic acid (EDTA), sorbitol, tartaric acid, phosphoric acid and the like.

In some embodiments, the total daily dose of the active compounds of the present invention administered to a subject in single or in divided doses can be in amounts, for example, from 0.01 to 25 mg/kg body weight or more usually from 0.1 to 15 mg/kg body weight. Single dose compositions may contain such amounts or submultiples thereof to make up the daily dose. In general, treatment regimens according to the present invention comprise administration to a human or other mammal in need of such treatment from about 1 mg to about 1000 mg of the active substance(s) of this invention per day in multiple doses or in a single dose of from 1 mg, 5 mg, 10 mg, 100 mg, 500 mg or 1000 mg.

In some embodiments, the agent is administered by intravenous, subcutaneous, intrathecal, intramuscular, inhalation (aerosol or mist), intracutaneous, transcutaneous, intragastric or oral administration.

In some embodiments, the agent that inhibits the activity of SUR1 is administered as a bolus injection. In some embodiments, the agent that inhibits the activity of SUR1 is administered as an infusion. In some embodiments, the agent that inhibits the activity of SUR1 is administered as a bolus injection in combination with an infusion. In some embodiments, the agent that inhibits the activity of SUR1 is administered as a loading dose followed by a constant infusion.

Liquid dosage forms for oral administration may include pharmaceutically acceptable emulsions, microemulsions, solutions, suspensions, syrups and elixirs containing inert diluents commonly used in the art, such as water, isotonic solutions, or saline. Such compositions may also comprise adjuvants, such as wetting agents; emulsifying and suspending agents; sweetening, flavoring and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulation can be sterilized, for example, by filtration through a bacteria-retaining filter, or by incorporating sterilizing agents in the form of sterile solid compositions, which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug, which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers, such as polylactide-polyglycoside. Depending on the ratio of drug to polymer and the composition of the polymer, the rate of drug release can be controlled. Examples of other biodegradable polymers include polyorthoesters and polyanhydrides. The depot injectables can also be made by entrapping the drug in liposomes or microemulsions, which are compatible with body tissues.

Suppositories for rectal administration of the drug can be prepared by mixing the drug with a suitable non-irritating excipient, such as cocoa butter and polyethylene glycol which are solid at ordinary temperature but liquid at the rectal temperature and will, therefore, melt in the rectum and release the drug.

Solid dosage forms for oral administration may include capsules, tablets, pills, powders, gelcaps and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, capsules, pills, and granules, aerosol for inhalation, can be prepared with coatings and shells such as enteric coatings and other coatings well known in the pharmaceutical formulating art. They may optionally contain opacifying agents and can also be of a composition that they release the active ingredient(s) only, or preferably, in a certain part of the intestinal tract, optionally in a delayed manner. Examples of embedding compositions which can be used include polymeric substances and waxes.

Dosage forms for topical or transdermal administration of a compound of this invention further include ointments, pastes, creams, lotions, gels, powders, solutions, sprays, inhalants or patches. Transdermal patches have the added advantage of providing controlled delivery of active compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel. The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

In one embodiment, the therapeutic compound is delivered transdermally. The term "transdermal delivery" as used herein means administration of the pharmaceutical composition topically to the skin wherein the active ingredient or its pharmaceutically acceptable salts, will be percutaneously delivered in a therapeutically effective amount.

In some embodiments, the composition to be applied transdermally further comprises an absorption enhancer. The term "absorption enhancer" as used herein means a compound which enhance the percutaneous absorption of drugs. These substances are sometimes also referred to as skin-penetration enhancers, accelerants, adjuvants and sorption promoters. Various absorption enhancers are known to be useful in transdermal drug delivery. U.S. Pat. Nos. 5,230,897, 4,863,970, 4,722,941, and 4,931,283 disclose some representative absorption enhancers used in transdermal compositions and for topical administration. In some embodiments, the absorption enhancer is N-lauroyl sarcosine, sodium octyl sulfate, methyl laurate, isopropyl myristate, oleic acid, glyceryl oleate or sodium lauryl sulfoacetate, or a combination thereof. In some embodiments, the composition contains on a weight/volume (w/v) basis the absorption enhancer in an amount of about 1-20%, 1-15%, 1-10% or 1-5%. In some embodiments, to enhance further the ability of the therapeutic agent(s) to penetrate the skin or mucosa, the composition can also contain a surfactant, an azone-like compound, an alcohol, a fatty acid or ester, or an aliphatic thiol.

In one embodiment, the therapeutic compound is delivered via a transdermal patch. In some embodiments, the invention provides a transdermal patch comprising an effective amount of the therapeutic compound, e.g., glibenclamide. In some embodiments, the transdermal patch further comprises an absorption enhancer.

In some embodiments, the transdermal composition can further comprise one or more additional excipients. Suitable excipients include without limitation solubilizers (e.g., $C_2$-$C_8$ alcohols), moisturizers or humectants (e.g., glycerol [glycerin], propylene glycol, amino acids and derivatives thereof, polyamino acids and derivatives thereof, and pyrrolidone carboxylic acids and salts and derivatives thereof), surfactants (e.g., sodium laureth sulfate and sorbitan monolaurate), emulsifiers (e.g., cetyl alcohol and stearyl alcohol), thickeners (e.g., methyl cellulose, ethyl cellulose, hydroxymethyl cellulose, hydroxypropyl cellulose, polyvinylpyrrolidone, polyvinyl alcohol and acrylic polymers), and formulation bases or carriers (e.g., polyethylene glycol as an ointment base). As a non-limiting example, the base or carrier of the composition can contain ethanol, propylene glycol and polyethylene glycol (e.g., PEG 300), and optionally an aqueous liquid (e.g., isotonic phosphate-buffered saline).

The method of the present invention employs the compounds identified herein for both in vitro and in vivo applications. For in vivo applications, the invention compounds can be incorporated into a pharmaceutically acceptable formulation for administration. Those of skill in the art can readily determine suitable dosage levels when the invention compounds are so used.

For the preparation of fluids for parenteral administration, suitable carriers include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of sterile water, or some other sterile injectable medium immediately before use. The active compound is admixed under sterile conditions with a pharmaceutically acceptable carrier and any needed preservatives or buffers as may be required.

The treatments may include various "unit doses." Unit dose is defined as containing a predetermined quantity of the therapeutic composition (an antagonist of the channel) calculated to produce the desired responses in association with its administration, e.g., the appropriate route and treatment regimen. The quantity to be administered, and the particular route and formulation, are within the skill of those in the clinical arts. Also of importance is the subject to be treated, in particular, the state of the subject and the protection desired. A unit dose need not be administered as a single injection but may comprise continuous infusion over a set period of time.

The preparation of a pharmaceutical composition that contains at least one therapeutically active agent or additional active ingredient(s) will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

The active agents may comprise different types of carriers depending on whether it is to be administered in solid, liquid or aerosol form, and whether it need to be sterile for such routes of administration as injection. The present invention can be administered intravenously, intradermally, transdermally, intrathecally, intraventricularly, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The active agents may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include active agents, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the active agents may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic and/or prophylactic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In some embodiments of the present invention, the active agents are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively, the compositions may be fashioned into a tablet or solution form that may be placed under the tongue or otherwise dissolved in the mouth.

Additional formulations that are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

In further embodiments, the active agents may be administered via a parenteral route. As used herein, the term "parenteral" includes routes that bypass the alimentary tract. Specifically, the pharmaceutical compositions disclosed herein may be administered for example, but not limited to intravenously, intradermally, transdermally, intramuscularly, intraarterially, intraventricularly, inhalation, intrathecally, subcutaneous, or intraperitoneally U.S. Pat. Nos. 6,7537, 514; 6,613,308; 5,466,468; 5,543,158; 5,641,515; and 5,399,363 (each specifically incorporated herein by reference in its entirety).

In some embodiments, the therapeutic compound is administered intrathecally. In some embodiments, the compound is administered intrathecally via an implantable pump. In one embodiment, the implantable pump comprises a SynchroMed™ II pump that stores and delivers medication into the intrathecal space (Medtronic).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, DMSO, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

In other embodiments, the active agents may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and laurocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroethylene support matrix is described in U.S. Pat. No. 5,780,045 (specifically incorporated herein by reference in its entirety).

The term aerosol refers to a colloidal system of finely divided solid or liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

All publications herein are incorporated by reference to the same extent as if each individual publication or patent application was specifically and individually indicated to be incorporated by reference.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLES

Example 1—Compositions and Methods for Treating Acute Respiratory Distress Syndrome It is shown herein in a rat model with mechanical ventilation alone, that treatment with glibenclamide reduces VILI. Moreover, it is shown that in a rat model of ARDS plus mechanical ventilation, treatment with glibenclamide reduces diffuse alveolar damage associated with pro-inflammatory concentrates and hemorrhagic pulmonary edema, and improves lung function.

The data described herein demonstrates that: (1) SUR1-TRPM4 is not present in the normal lung; (2) SUR1-TRPM4 is newly upregulated in the diseased/ventilated lung; (3) in the diseased/ventilated lung, blockade of SUR1-TRPM4 by glibenclamide reduces diffuse alveolar damage associated with pro-inflammatory concentrates and hemorrhagic pulmonary edema, and improves lung function.

Rat Models of Lung Injury and their Treatment

In some cases, a rat model of mechanical ventilation alone was used, in which other major stressors (e.g., major surgery, infection, etc.) are eliminated, in order to investigate the effects of ventilation by itself on lung function. Rats that were otherwise uninjured received mechanical ventilation for 4 hours with a tidal volume of 10 mL/kg. Adequate ventilation was confirmed by arterial blood gas analysis with values within normal limits. Rats were euthanized at 24 hours.

In other cases, a rat model of ARDS was used in which acute lung injury is induced by acid instillation, followed by mechanical ventilation. The acid aspiration model is known to create both respiratory and inflammatory responses, and is considered to be the most clinically applicable model to study the intermediate-term effects of ventilator-associated lung injury in rats (Henzler et al., Anesth Analg, (2011), 112(5):1139-46). After inducing acute lung injury as described, rats received mechanical ventilation for 4 hours with a tidal volume of 8-10 mL/kg. Rats were euthanized at 4 or 24 hours (Puig, et al., Am J Physiol Lung Cell Mol Physiol, (2016), 311(2), PubMed PMID: 27317688).

In these models, treatment with vehicle vs. glibenclamide was compared, a potent inhibitor of SUR1-TRPM4 channels. Glibenclamide was administered at a dose of 10-50 μg/kg IP, at the onset of MV, and in some case at 6 hours.

SUR1-TRPM4 Channels are Upregulated in a Rat Models VILI

The SUR1-TRPM4 (sulfonylurea receptor 1—transient receptor potential melastatin 4) channel has been described in the central nervous system (CNS) (Simard et al., Nat Med, (2006), 12(4):433-40, PubMed PMID: 16550187; Simard et al., Stroke, (2010), 41(3):531-7, PubMed PMID: 20093633). In the CNS, SUR1-TRPM4 channels are not constitutively expressed, but are transcriptionally upregulated de novo under conditions of ischemia/hypoxia and inflammation, in part via NF-kappaB activation (Gerzanich et al., PLoS One, (2018), 13(4):e0195526).

Figure 1:
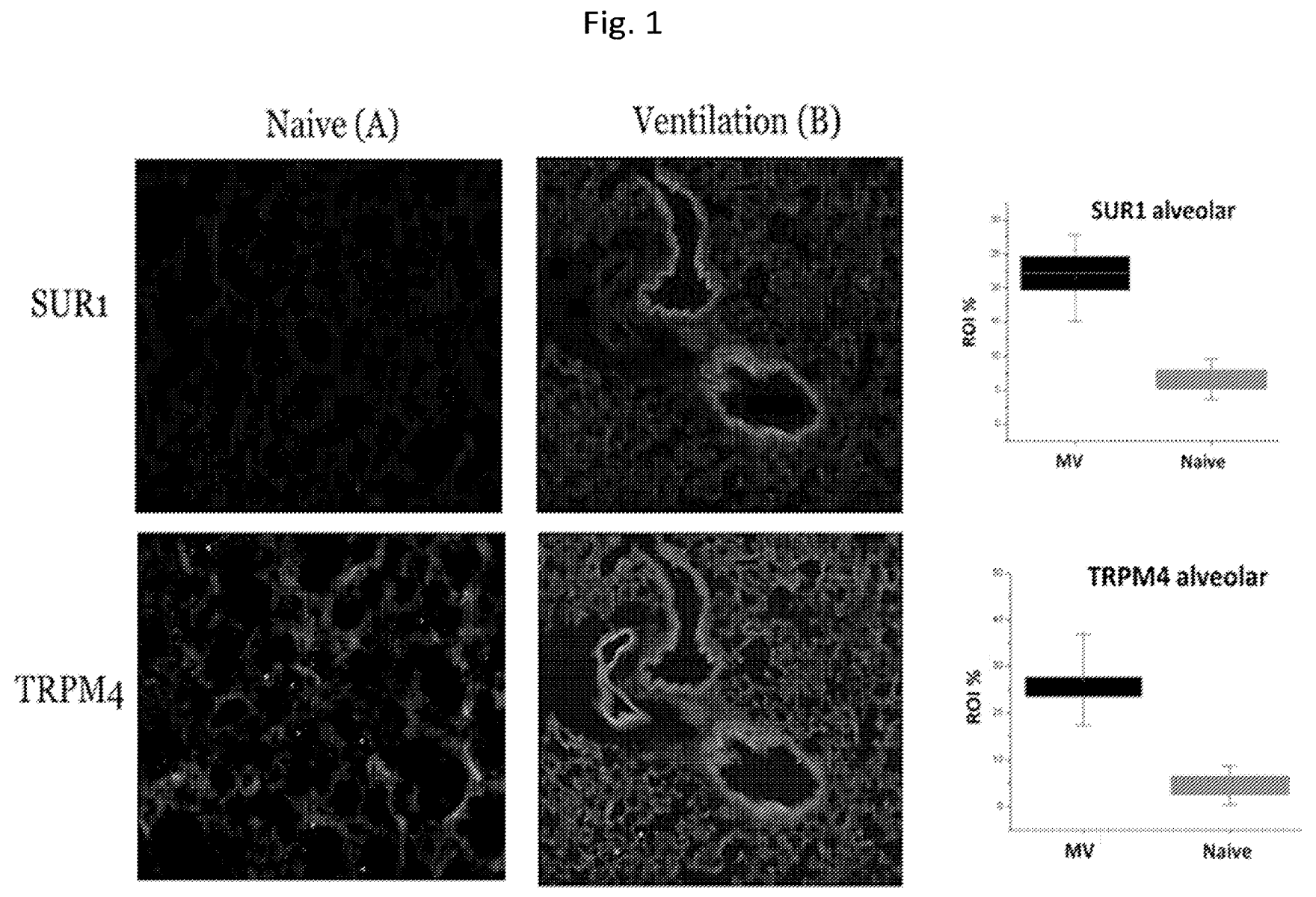
Figure 3:
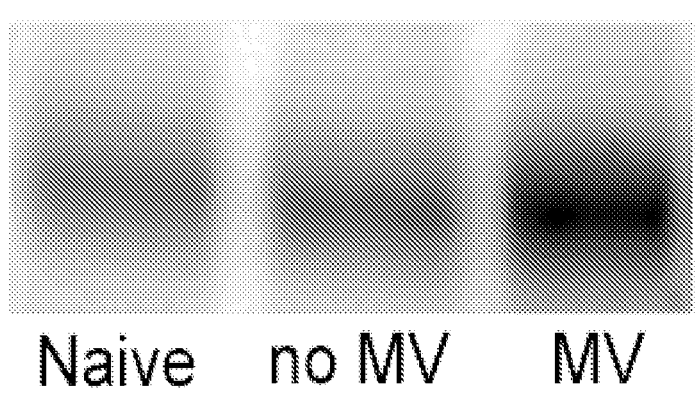
FIG. 3 Mechanical ventilation (MV) induces upregulation of SUR1 in the lung. Immunoblot for SUR1 of lung tissue from a naïve, non-ventilated rat (naïve), a rat intubated but not ventilated (no MV) and a rat that was intubated and underwent mechanical ventilation (tidal volume, 10 mL/kg) for 4 hours, and was euthanized at 24 hours (MV).

The SUR1-TRPM4 channel has not been reported in the lungs or elsewhere outside the CNS. Immunohistochemistry was performed on lung tissues in the MV model of VILI. In lungs from MV rats, expression of SUR1 and TRPM4 was identified in alveolar epithelium (FIG. 1) and in vascular endothelium (FIG. 2). Quantification of the immunohisto-chemistry data indicated that the expression of SUR1 was significantly increased in lungs from MV rats, whereas it was essentially absent in the lungs from "naïve" rats without MV (FIG. 1, 2). The upregulation of SUR1 by MV was confirmed by immunoblot (FIG. 3). Additionally, quantifi-cation of the immunohistochemistry data indicated that the expression of TRPM4 was significantly increased in lungs from MV rats, whereas it was present, albeit in lesser amounts, in the lungs from "naïve" rats without MV (FIG. 1, 2).

These data are the first to show de novo upregulation of SUR1-TRPM4 as a feature of VILI following MV.

Glibenclamide Reduces VILI-Associated Pulmonary Edema

Figure 4:
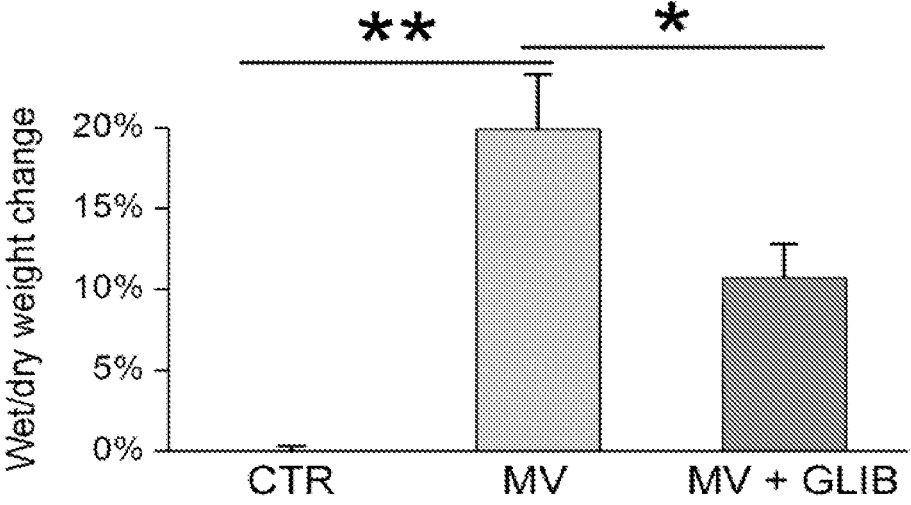
FIG. 4. Glibenclamide reduces pulmonary edema caused by 4 hours of mechanical ventilation (MV), assessed at 24 hours. Pulmonary edema was quantified as the ratio of wet weight to dry weight, normalized to that in naïve controls (CTR) and expressed as a percent. MV (tidal volume, 10 mL/kg) induced significant pulmonary edema, which was significantly reduced by treatment with glibenclamide (10 µg/kg IP); *, $P<0.05$; **, $P<0.01$.

VILI is known to be associated with pulmonary edema. Experiments were performed to examine the effect of glib-enclamide on VILI-associated pulmonary edema in other-wise uninjured rats. At the start of MV (10 mL/kg), rats were administered glibenclamide, 10 µg/kg IP or vehicle. MV continued for 4 hours, and rats were euthanized at 24 hours. Glibenclamide significantly decreased pulmonary edema in this model (FIG. 4).

Glibenclamide Improves Pulmonary Function in ARDS with Ventilation

Experiments were performed to examine the effect of glibenclamide on lung function in a rat model of ARDS with MV. The ARDS model involved acute lung injury in intu-bated rats induced by intratracheal instillation of HCL (0.1 N; 1.2 mL/kg), followed by MV (8 mL/kg) (Puig, et al., Am J Physiol Lung Cell Mol Physiol, (2016), 311(2), PubMed PMID: 27317688). Rats were administered either glibencl-amide (50 µg/kg IP at the onset of MV and at 6 hours) or vehicle. MV was continued for 4 hours, and rats were euthanized at 24 hours.

Vehicle treatment was associated at 24 hours with a "beefy" appearance of the lungs due to hemorrhagic exu-dates and hemorrhagic pulmonary edema, as previously reported (Paris et al., PLoS One, (2019), 14(4):e0202456; Tavares et al., J Vis Exp, (2019), (150), PubMed PMID: 31524861). Glibenclamide treatment reduced hemorrhagic exudates, yielding a less beefy appearance of the lungs. Pulse oximetry at 24 hours showed reduced oxygen satura-tion with vehicle treatment (sO$_2$ for VEH=78±2.6%; n=3) that was improved with glibenclamide (sO$_2$ for GLIB=88±4.4%; n=3).

Example 2—Development of Glibenclamide to Mitigate Respiratory Dysfunction and Study of a Novel Pathway Involving SUR1 in Trafficking and Exocytosis of MRP8/14

Rat models of lung injury. The effects of glibenclamide using two conventional models, one of VILI, one of ARDS were studied.

Nevertheless, in the first experiment, a conventional rat model of VILI with MV alone was used, in otherwise uninjured rats. MV was performed using a small animal ventilator (Harvard Apparatus), with F$_i$O$_2$ of 0.21, respira-tory rate of 60 breaths/min, tidal volumes (V$_T$)=10 mL/kg, and positive end-expiratory pressure (PEEP) of 2 cm H$_2$O. Rats were anesthetized, intubated, and received MV for 4 hours. Adequate ventilation was confirmed by arterial blood gas analysis, with values within normal limits. Rats were euthanized at 24 hours.

In a second experiment, a conventional rat model of ARDS plus MV was used. Rats were anesthetized and intubated. ALI was induced by intratracheal instillation of HCL (0.1 N; 1.2 mL/kg, with half the volume delivered in the right lateral and the other half in the left lateral decubitus positions) (Puig et al., Am J Physiol Lung Cell Mol Physiol, (2016), 311:L229-37). After inducing ALI, rats received MV for 4 hours, as above, except that V$_T$=8 mL/kg. Rats were euthanized at 24 hours.

Treatment with glibenclamide. In these experiments, treatment with vehicle (VEH) vs. glibenclamide (GLIB) was compared. Since the goal was to target SUR1, not NLRP3, low-dose glibenclamide (10-50 µg/kg IP) was used, admin-istered at the onset of MV, and in some cases, with a second dose administered at 6 hours.

SUR1 upregulation in epithelium and neutrophils in VILI. The SUR1-TRPM4 channel was first described by us in the CNS, but has not been reported in the lungs or elsewhere outside the CNS (Simard et al., Nat Med, (2006), 12:433-40; Simard et al., Stroke, (2010), 41:531-7).

Figure 5:
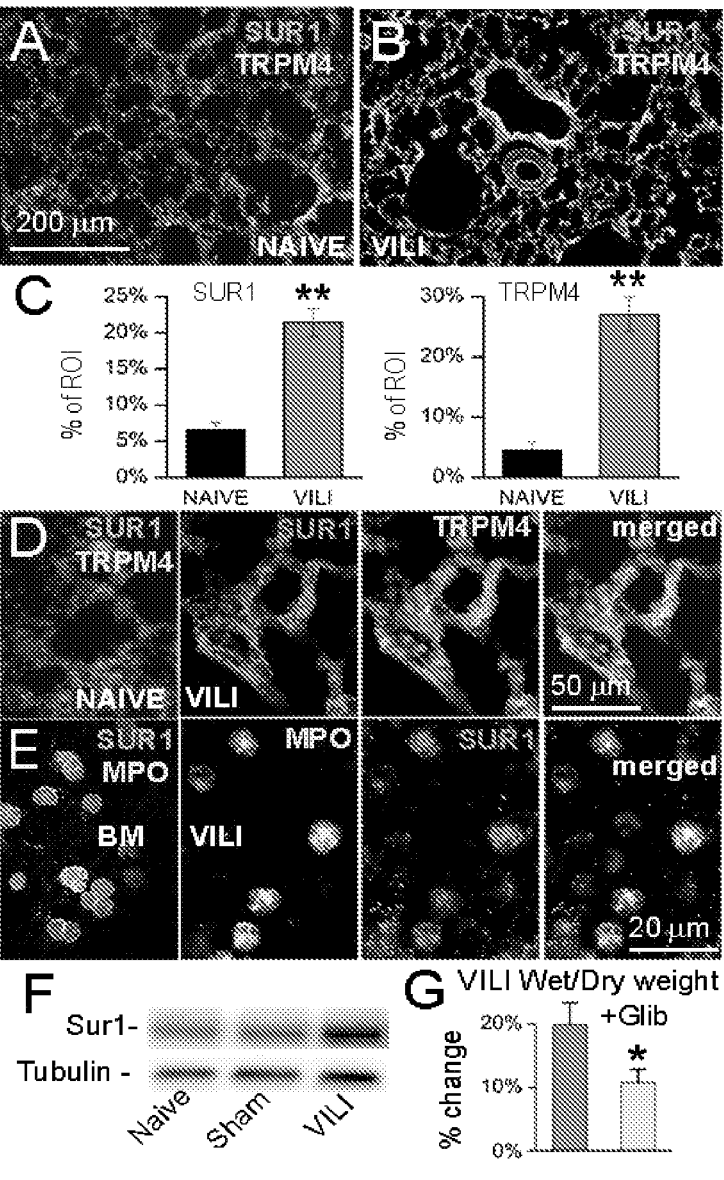
FIG. 5. SUR1 upregulation in epithelium and neutrophils in VILI. A,B,D,E: Immunohistochemistry (IH) of uninjured (naïve) lung (A, D), of bone marrow (BM) neutrophils (E), of VILI lung (B,D) and neutrophils after tissue invasion (E), immunolabeled for SUR1, TRPM4 and myeloperoxidase (MPO), as indicated. C: Quantification of IH data. F: Immunoblot of lung tissue for SUR1 (tubulin as loading control). G: Pulmonary edema, measured as wet weight/dry weight, in VILI lungs with VEH vs. GLIB treatment (3/group); *, $P<0.05$.

Immunohistochemistry was performed on lung tissues. Abundant expression of SUR1 and TRPM4 was identified in alveolar epithelium and vascular endothelium in the VILI model, compared to control (FIG. 5A,B). Quantification showed that the expression of SUR1 and TRPM4 were significantly upregulated in lungs from VILI rats (FIG. 5C). Upregulation of SUR1 due to MV was confirmed by immu-noblot (FIG. 5F).

High magnification views showed prominent co-localiza-tion of SUR1 and TRPM4 in alveolar epithelium of VILI rats (FIG. 5D). In addition, activated, MPO+ neutrophils recruited to sites tissue injury uniformly expressed SUR1, whereas immature (quiescent), MPO+ neutrophils in bone marrow do not express SUR1 (FIG. 5E). De novo upregu-lation of SUR1 in epithelium and neutrophils is a novel feature of VILI.

Glibenclamide reduces VILI-associated pulmonary edema. The effect of glibenclamide on VILI-associated pulmonary edema was examined. At the start of MV (V$_T$=10 mL/kg), rats were administered glibenclamide, 10 µg/kg IP or vehicle. MV was continued for 4 hours, and rats were euthanized at 24 hours. Measurement of wet weight/dry weight showed that GLIB significantly decreased pulmo-nary edema compared to VEH (FIG. 5G).

Glibenclamide improves lung function in ARDS with MV. Experiments were performed to examine the effect of glibenclamide on lung function in the model of ARDS with acid-induced ALI. Rats were administered either VEH or GLIB (50 µg/kg IP at the onset of MV and at 6 hours). MV (V$_T$=8 mL/kg) was continued for 4 hours, following which rats were extubated, recovered from anesthesia and returned to their home cages.

Figure 6:
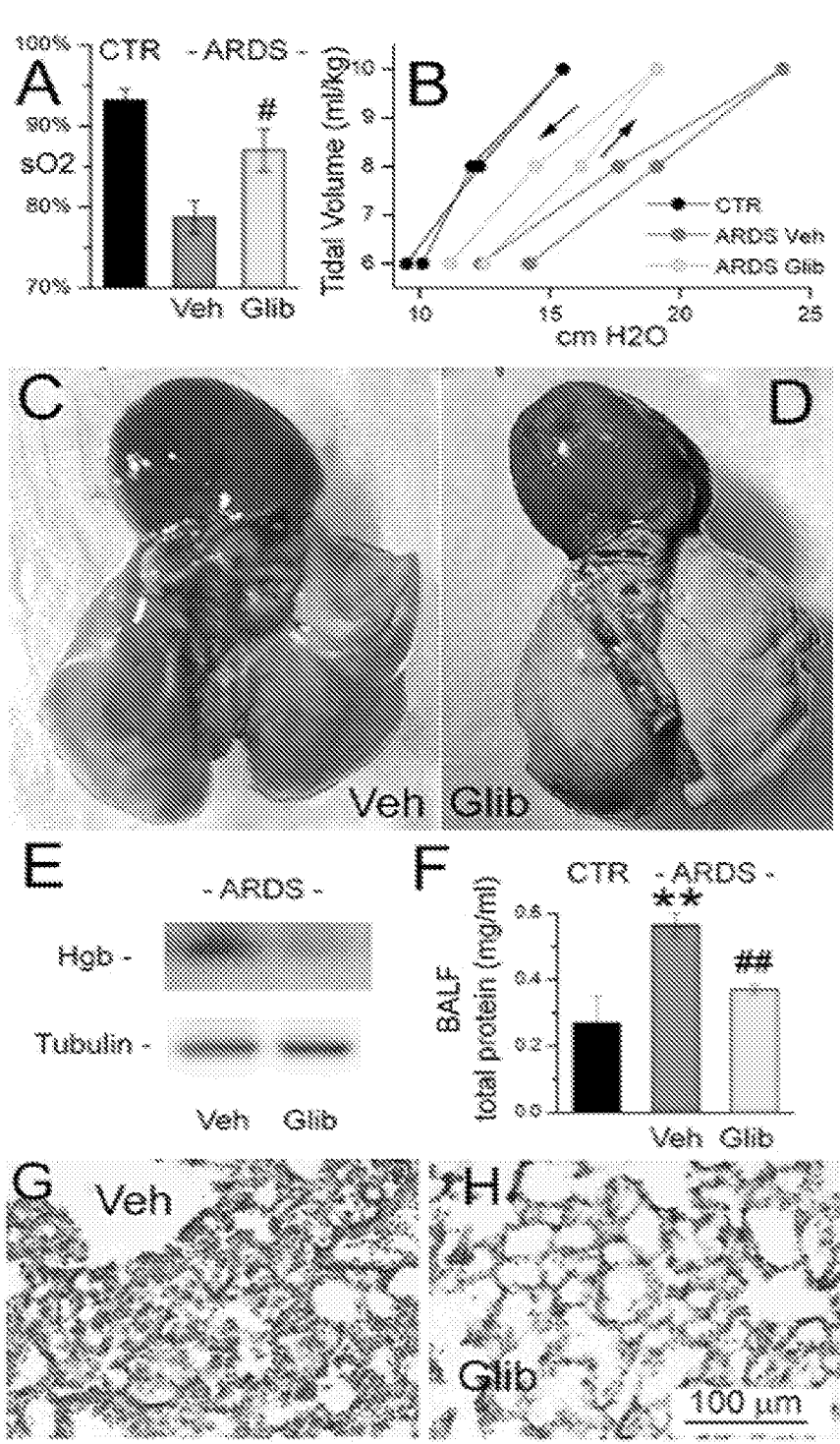
FIG. 6. Glibenclamide improves lung function and reduces cellular infiltrates in ARDS with MV. A: $sO_2$ at 24 hours (spontaneous ventilation); (3/group); #, $P<0.05$. B: Volume-pressure curves showing dynamic lung compliance in control and ARDS model with VEH or GLIB treatment; (2/group). C,D: Gross appearance of lungs in ARDS model with VEH or GLIB treatment; (representative of 6/group). E,F: Immunoblot for hemoglobin (Hgb) in lung or protein in BALF in ARDS with VEH or GLIB treatment; (3/group); ** and ##, $P<0.01$. G,H: H&E sections of lung in ARDS model with VEH or GLIB treatment; (representative of 6/group).

Lung function was evaluated at 24 hours. Rats were re-anesthetized. Pulse oximetry showed reduced oxygen saturation in rats with VEH-treatment (sO$_2$ for VEH=78±2.6%; n=3) that was less impaired with GLIB-treatment (sO$_2$ for GLIB=88±4.4%; n=3) (FIG. 6A).

Rats were then re-intubated for MV. Volume-controlled dynamic lung compliance (C$_{dyn}$) measurements were per-formed by recording peak inspiratory pressures (PIP) required to achieve V$_T$=6, 8, 10, 8, 6 mL/kg, in successive steps of 5 min each. C$_{dyn}$ is calculated as V$_T$/(PIP-PEEP)

(Henzler D et al., Intensive Care Med Exp, (2019), 7:60). Pressure-volume curves are shown in FIG. 6B. Compared to uninjured controls (FIG. 6B, black), the pressure-volume curve for ARDS rats administered VEH exhibited hysteresis and was markedly shifted to the right (FIG. 6B, red), similar to observations in humans with ARDS (Moloney et al., Br J Anaesth, (2004), 92:261-70). By contrast, in ARDS rats administered GLIB, the shift to the right was less pronounced (FIG. 6B, green).

Post-mortem examination of the lungs showed that in ARDS rats, VEH treatment was associated with a "beefy" appearance of the lungs due to hemorrhagic exudates and hemorrhagic pulmonary edema (FIG. 6C), as previously reported (Paris et al., PLoS One, (2019), 14:e0202456; Tavares et al., J Vis Exp, (2019), 30: (150): 10.3791/60024). GLIB treatment reduced hemorrhagic exudates, yielding a less beefy appearance of the lungs (FIG. 6D). Immunoblot of lung tissues for hemoglobin (Hgb) confirmed less hemorrhagic exudate in ARDS rats administered GLIB (FIG. 6E).

In a subgroup of rats, after completing the 24-hour lung function assessments, rats were euthanized, and the lungs were lavaged using 5 mL normal saline to obtain bronchio-alveolar lavage fluid (BALF). BALF was analyzed for protein. Protein in BALF from ARDS rats administered VEH was markedly increased, whereas in ARDS rats administered GLIB, the increase was less pronounced (FIG. 6F).

Histological examination of hematoxylin and eosin (H&E)-stained lung sections showed that GLIB treatment was associated with reduced cellular infiltrates compared to VEH treatment (FIG. 6G,H).

Figure 7:
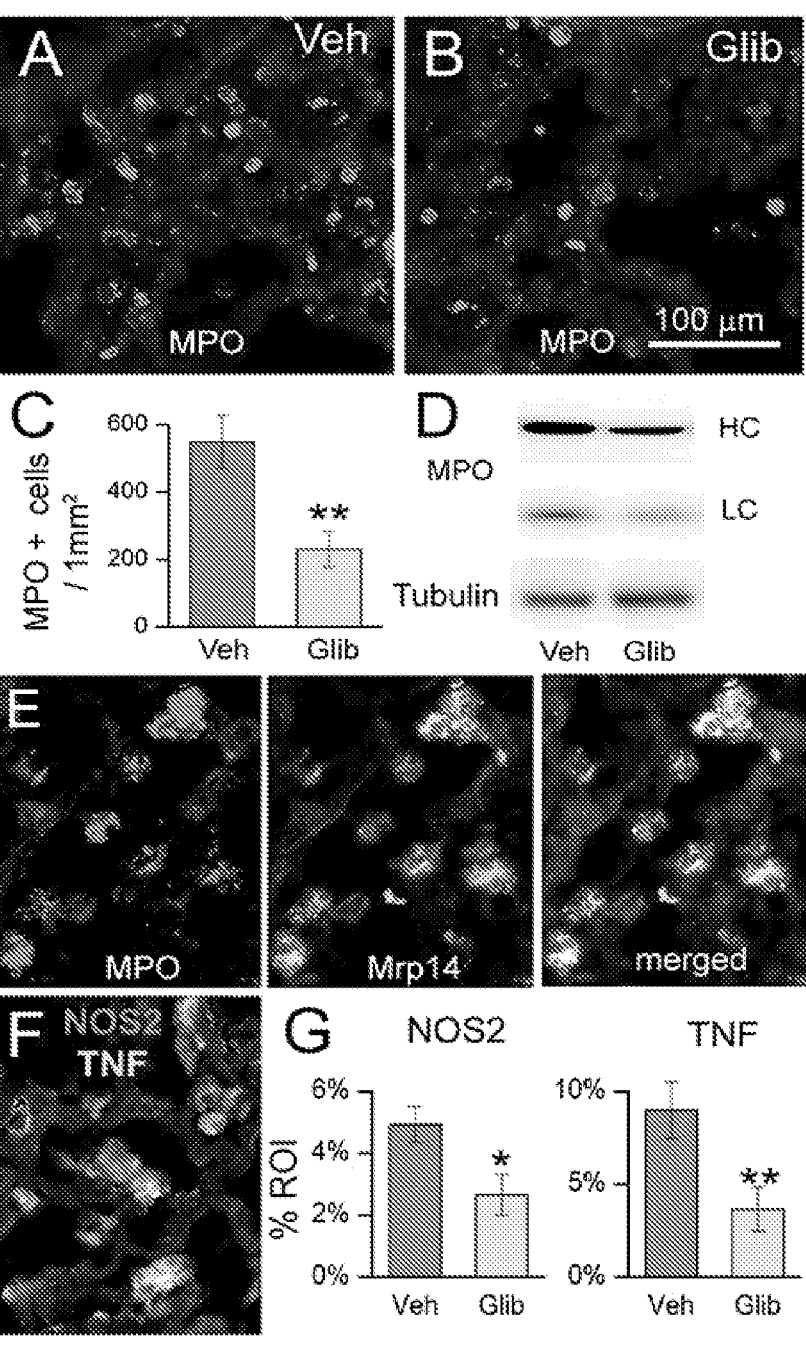
FIG. 7. Glibenclamide reduces inflammation in ARDS with MV. A-D: Immunolabeling for and quantification of MPO in ARDS model with VEH or GLIB treatment; (4/group); **, $P<0.01$; blot shows both high MW (HC) and low MW (LC) chain for MPO. E: MPO and MRP14 co-localize in neutrophils. F,G: Immunolabeling for and quantification of NOS2 and TNF in ARDS model with VEH or GLIB treatment; (4/group); *, $P<0.05$; **, $P<0.01$.

Glibenclamide reduces neutrophil invasion and other markers of inflammation. Lung tissues were examined for markers of inflammation, including neutrophils. Immuno-histochemistry for myeloperoxidase (MPO) showed abundant neutrophil invasion in VEH-treated rats that was less pronounced in GLIB-treated rats (FIG. 7A,B). Quantification of MPO by immunohistochemistry and by immunoblot confirmed significant reduction with GLIB (FIG. 7C,D). As expected, MPO activity co-localized with MRP14, consistent with neutrophil expression of MRP14 (FIG. 7E). Additionally, both NOS2 expression and TNF expression in lung tissues were attenuated by GLIB treatment (FIG. 7F,G).

Figure 8:
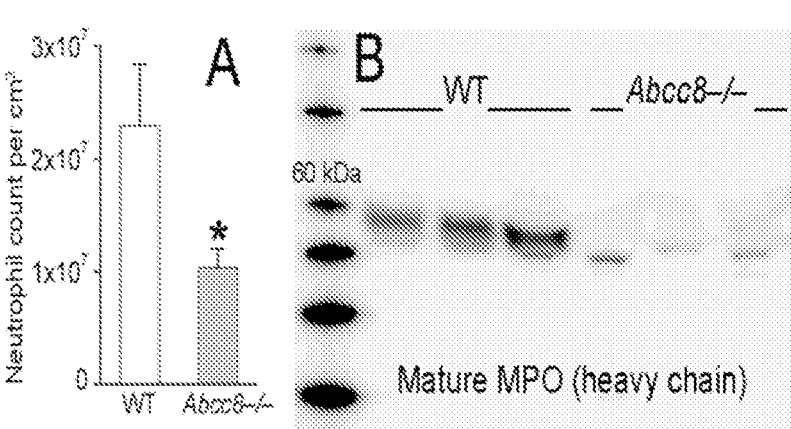
FIG. 8. Intraperitoneal (IP) injection of CXCL8 (1 mg in 20 ml) in Abcc8−/− mice results in less neutrophil recruitment (A) and less neutrophil degranulation, measured by MPO protein (B), at 4 hr in IP lavage fluid, compared to WT mice; 3 mice/group); *, $P<0.05$.

SUR1 is critical for neutrophil recruitment. Abcc8–/– mice were used, which lack SUR1, to examine the role of SUR1 in neutrophil recruitment. CXCR2 ligand and potent neutrophil attractant, CXCL8, was injected into the peritoneal cavity. Peritoneal lavage fluid was collected 4 hr later to count neutrophils and to measure MPO. Both measures were significantly reduced in Abcc8–/– compared to WT mice (FIG. 8).

Figure 11:
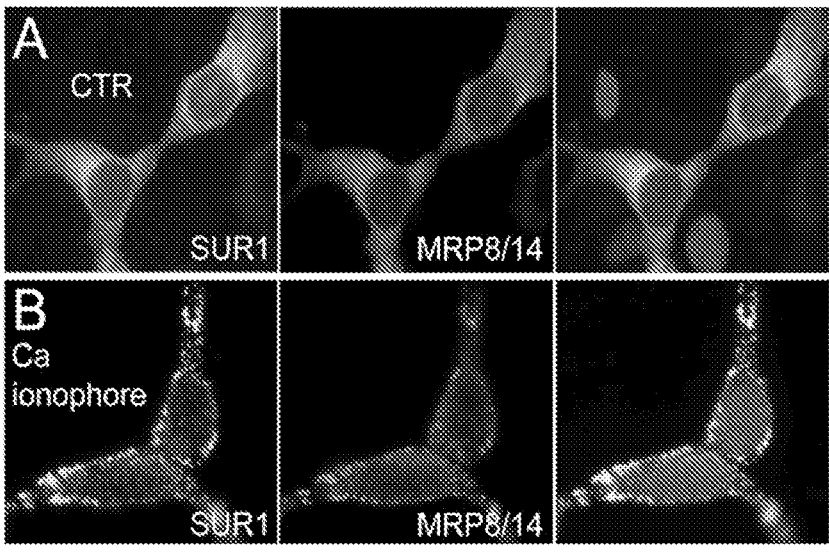
FIG. 11. Calcium-induced co-translocation of SUR1 and MRP8/14. Images of HEK-293 cells co-transfected with SUR1 and MRP8/14 and labeled with anti-SUR1 antibody (green) and anti-MRP8/14 antibody (red); superimposed images with DAPI-labeled nuclei are shown on the right. Note the diffuse cytoplasmic distribution of MRP8/14 proteins under control conditions (A), and the translocation of SUR1 and MRP8/14 proteins to granular structures beneath the cell membrane after activation by the $Ca^{2+}$ ionophore, A23187 (B); images representative of >10 experiments.

MRP8/14 translocation to the plasma membrane. In resting cells, MRP8/14 are localized in the cytoplasm (see FIG. 11A). An increase in intracellular $Ca^{2+}$ leads to translocation of MRP8/14 to cytoskeletal components and plasma membrane (see FIG. 11B) (Van den Bos et al., J Immunol, (1996), 156:1247-54; Roth et al., Blood, (1993), 82:1875-83; Bhardwaj et al., Eur J Immunol, (1992), 22:1891-7). However, mechanisms by which MRP8/14 traffic to and exit the neutrophil cell membrane are poorly understood.

As cytoplasmic proteins, MRP8/14 lack a transmembrane leader signal, and therefore cannot be secreted via the classical Golgi-associated pathway (Ehrchen et al., J Leukoc Biol, (2009), 86:557-66; Kerkhoff et al., Biochim Biophys Acta, (1998), 1448:200-11). MRP8/14 may acquire the required transmembrane component by co-associating with SUR1, which is a transmembrane protein. This is based on the fact that a similar function is performed by SUR1 when it co-associates with Kir6.2 to permit trafficking of $K_{ATP}$ to the cell membrane (Sharma N, J Biol Chem, (1999), 274: 20628-32; Aguilar-Bryan, Endocr Rev, (1999), 20:101-35. This predicts that by co-associating with MRP8/14, the 'RKR' endoplasmic reticulum (ER) retention signal located near the C-terminus of SUR1 becomes 'shielded', allowing SUR1 to leave the ER and traffic to secondary granule membrane, carrying MRP8/14 with it.

Figure 9:
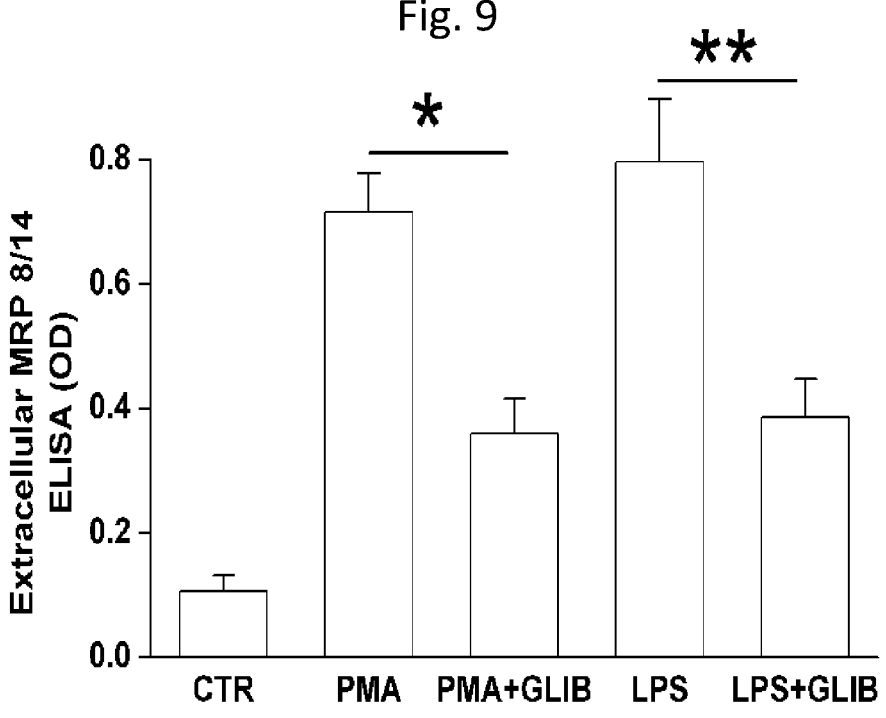
FIG. 9. Glibenclamide reduces MRP8/14 exocytosis from activated human neutrophils. Bar graph of the release of the MRP8/14 detected using ELISA in extracellular media in control neutrophils (CTR), neutrophils stimulated with PKC activator, phorbol 12-myristate 13-acetate (PMA), and lipopolysaccharide (LPS), both alone and with 30 M glib-enclamide (PMA+GLIB and LPS+GLIB); n=6; *$P<0.05$; **$P<0.01$.
Figure 10:
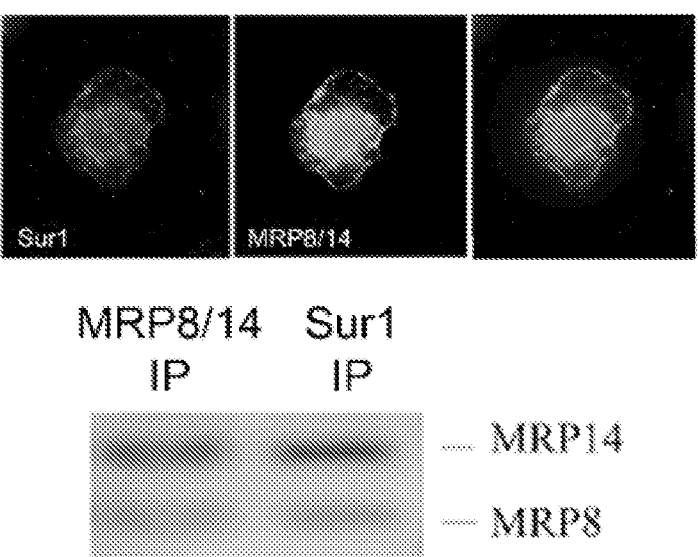
FIG. 10. Co-association of SUR1 and MRP8/14 in activated human neutrophils. Top: SUR1 (red) and MRP8/14 (green) co-localize in human neutrophils (yellow, right). Bottom: Immunoblot of human neutrophils showing that MRP8 and MRP14 co-immunoprecipitate with anti-SUR1 antibody (SUR1 IP). Left: positive control for MRP8 and MRP14.

Glibenclamide inhibits MRP8/14 exocytosis. Exocytosis of MRP8/14 from human neutrophils using ELISA was studied. Neutrophil activation by phorbol myristate acetate (PMA) or lipopolysaccharide (LPS) resulted in robust release of MRP8/14 (FIG. 9) (Faurschou et al., Microbes Infect, (2003), 5:1317-27). However, MRP8/14 exocytosis following application of either stimulus was significantly reduced by co-incubating with glibenclamide (FIG. 9). Co-immunoprecipitation experiments were performed to determine whether SUR1 and MRP8/14 physically co-associate. Immuno-isolation using anti-SUR1 antibody resulted in 'pull-down' of MRP8/14 (FIG. 10), consistent with physical interaction between SUR1 and MRP8/14.

Figure 12:
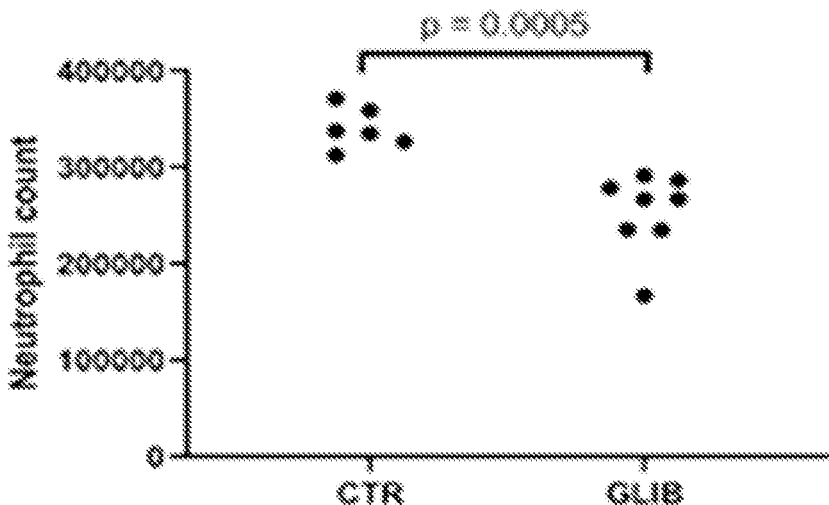
FIG. 12. Neutrophils in BALF. At 24 hours after LPS-induced ARDS, bronchioalveolar fluid (BALF) was collected and analyzed for neutrophil counts. Compared to vehicle-treated controls, mice treated with glibenclamide (GLIB) showed a significant reduction in neutrophils.

SUR1 and MRP8/14 functionally interact. HEK-293 cells heterologously co-expressing SUR1 and MRP8/14 were used. When cells heterologously co-expressing SUR1 and MRP8/14 were activated by $Ca^{2+}$ influx using the ionophore, A23187, the proteins became rearranged intracellularly: before activation, MRP8/14 was diffusely localized in the cytoplasm; after activation, MRP8/14, accompanied by SUR1, translocated to granular structures beneath the cell membrane (FIG. 12), consistent with a functional interaction between SUR1 and MRP8/14 (Stroncek et al., J Transl Med, (2005), 3:36). Importantly, this experiment suggests that, by co-associating with MRP8/14, the endoplasmic reticulum (ER) retention signal, 'RK R', near the C-terminus of SUR1 becomes shielded, allowing SUR1 to traffic from ER to granules beneath the cell membrane, accompanied by MRP8/14. Together, these data lead to the novel hypothesis that SUR1 plays an important role as chaperone in intracellular trafficking of MRP8/14, which is required for MRP8/14 release from activated neutrophils.

Example 3—Glibenclamide Reduces Infiltration of Neutrophils and Pro-Inflammatory Cytokines, IL-6 and MCP-1 in Lung Tissues The inflammatory response in the lungs to irritants and pathogens such as toxic chemicals, bacteria and viruses, including the SARS-CoV-2 virus, is a natural response aimed at neutralizing the harmful agent. An important component of the inflammatory response includes infiltration of neutrophils, typically recruited to tissues by cytokines such as MCP-1. However, the natural inflammatory response can be overexuberant, leading to secondary injury to lung tissues. Thus, dampening but not extinguishing the inflammatory response in the lungs under certain pathological conditions may be a desirable therapeutic goal.

A conventional mouse model of acute respiratory distress syndrome (ARDS), induced by infusion of lipopolysaccharide (LPS; 0.25 mg/kg intratracheal) into the lungs, was used to investigate the effects of glibenclamide on the inflammatory response in the lungs. Glibenclamide (10 µg IP) vs. vehicle was administered 2 hours after LPS and a second time 5 hours later.

Figure 13:
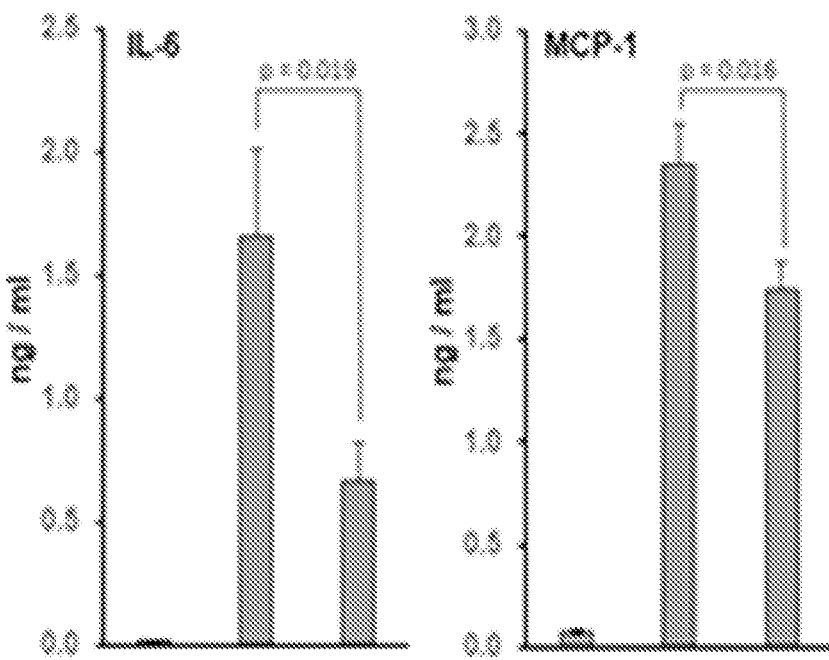
FIG. 13. Cytokines in lung tissues. At 24 hours after LPS-induced ARDS, lung tissues were harvested and analyzed for IL-6 and MCP-1. Levels of IL-6 and MCP-1 were minimal in lung tissues from uninjured sham animals (left-most bar in both panels). Compared to vehicle-treated controls (middle bar in both panels), mice treated with glibenclamide showed a significant reduction in both IL-6 and MCP-1 (rightmost bar in both panels).

At 24 hours after LPS induction, bronchioalveolar fluid (BALF) was analyzed for neutrophil infiltration, and lung tissues were analyzed for cytokine expression. Glibenclamide treatment was associated with a significant reduction in neutrophils in BALF (FIG. 12), and significant reductions in the pro-inflammatory cytokines, IL-6 and MCP-1 in lung tissues (FIG. 13).

MRP8/14 is a major cytoplasmic protein complex in neutrophils that is important for neutrophil function, including tissue invasion by neutrophils.

The LPS-induced mouse model of ARDS was used to investigate the effect of glibenclamide on the release of MRP8 (a.k.a., S100A8). Glibenclamide (10 μg IP) vs. vehicle was administered 2 hours after LPS and a second time 5 hours later.

Figure 14:
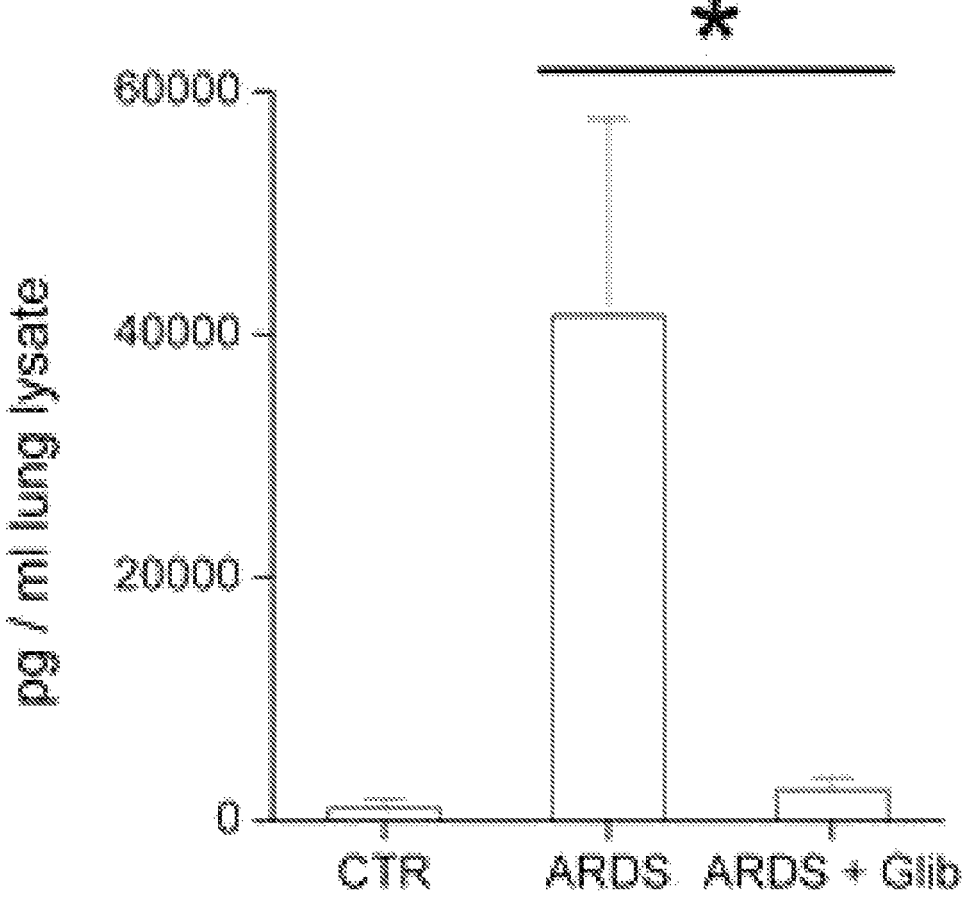
FIG. 14. S100A8/MRP8 in lung tissues. At 24 hours after LPS-induced ARDS, lung tissues were harvested and analyzed for S100A8/MRP8. Levels of S100A8/MRP8 were minimal in lung tissues from uninjured sham animals (left-most bar). Compared to vehicle-treated controls (middle bar), mice treated with glibenclamide showed a significant reduction in S100A8/MRP8 (rightmost bar).

At 24 hours after LPS induction, bronchioalveolar fluid (BALF) was analyzed for neutrophil infiltration, and lung tissues were analyzed for S100A8/MRP8, which is released by neutrophils. As previously, LPS instilled into the lungs caused a massive invasion of neutrophils into the BALF, as well as dramatic accumulation of the S100A8/MRP8. Glibenclamide treatment was associated with a significant reduction in neutrophils in BALF (as shown previously in FIG. 12), and a significant reduction in S100A8/MRP8 in lung tissues, almost to the level in control animals (FIG. 14).

We claim:

1. A method of treating acute lung injury in a human subject in need thereof, comprising administering to the subject an effective amount of an agent that inhibits the activity of SUR1, wherein the agent is glibenclamide, wherein glibenclamide is administered to the subject in an amount of between about 0.5 mg/day to about 10 mg/day, wherein the subject is on a mechanical ventilator.

2. The method of claim 1, wherein the lung injury is associated with acute respiratory distress syndrome (ARDS).

3. The method of claim 1, wherein the lung injury is ventilator induced lung injury (VILI).

4. The method of claim 1, wherein the subject has coronavirus infection.

5. The method of claim 1, wherein the subject is infected with a pathogen.

6. The method of claim 1, wherein SUR1 is contained in a complex.

7. The method of claim 1, wherein the SUR1 containing complex comprises a SUR1-TRPM4 channel.

8. The method of claim 1, wherein the SUR1 containing complex comprises SUR1 and MRP8/14.

9. The method of claim 1, wherein the agent that inhibits the activity of SUR1 is administered as a bolus injection, an infusion, or as a bolus injection in combination with an infusion.

10. The method of claim 1, wherein the agent that inhibits the activity of SUR1 is administered as a loading dose followed by a constant infusion.

* * * * *